(12) United States Patent
Suh et al.

(10) Patent No.: US 8,242,152 B2
(45) Date of Patent: *Aug. 14, 2012

(54) USE OF 4-[(4-THIAZOLYL)PHENOXY] ALKOXY-BENZAMIDINE DERIVATIVES FOR THE PROPHYLAXIS AND TREATMENT OF OSTEOPOROSIS

(75) Inventors: Hong-Suk Suh, Kumjung-Gu (KR); Jin Soo Lee, Yongin-si (KR); Pan-Soo Kim, Anyang-i si (KR); Yun-Ha Hwang, Ansan-si (KR); Jei Man Ryu, Anyang-si (KR); Yong-Ho Chung, Anyang-si (KR); Eun-Joo Kim, Yusong-gu (KR); Do-Hui Kim, Songnam-si (KR); Yong-Youp Park, Kumjung-gu (KR)

(73) Assignee: Dong Wha Pharmaceutical Co., Ltd., Seoul (KR)

( * ) Notice: Subject to any disclaimer, the term of this patent is extended or adjusted under 35 U.S.C. 154(b) by 390 days.

This patent is subject to a terminal disclaimer.

(21) Appl. No.: 12/689,884

(22) Filed: Jan. 19, 2010

(65) Prior Publication Data
US 2010/0160394 A1    Jun. 24, 2010

Related U.S. Application Data

(63) Continuation-in-part of application No. 10/484,094, filed as application No. PCT/KR02/00463 on Mar. 19, 2002, now Pat. No. 7,662,840.

(30) Foreign Application Priority Data

Jul. 19, 2001 (KR) .................................. 2001-43490

(51) Int. Cl.
| | |
|---|---|
| *A01N 43/78* | (2006.01) |
| *A01N 37/52* | (2006.01) |
| *A61K 31/425* | (2006.01) |
| *A61K 31/155* | (2006.01) |
| *C07D 277/60* | (2006.01) |
| *C07D 416/00* | (2006.01) |
| *C07C 249/00* | (2006.01) |
| *C07C 251/00* | (2006.01) |
| *C07C 259/00* | (2006.01) |
| *C07C 291/00* | (2006.01) |

(52) U.S. Cl. ........ 514/365; 514/631; 514/878; 548/150; 564/229

(58) Field of Classification Search .................. 514/365, 514/366, 631, 878; 548/146, 150; 564/225, 564/229; 562/440
See application file for complete search history.

(56) References Cited

U.S. PATENT DOCUMENTS
| | | | |
|---|---|---|---|
| 5,451,700 | A | 9/1995 | Morrissey et al. |
| 6,150,390 | A | 11/2000 | Suh et al. |

FOREIGN PATENT DOCUMENTS
| | | |
|---|---|---|
| AU | 2002241361 | 5/2007 |
| EP | 02707300 | 2/2007 |
| KR | 98-071076 | 10/1998 |
| KR | 10-0454767 | 10/2004 |

OTHER PUBLICATIONS

Ford-Hutchinson, A.W., et al., Nature (London), 286, 264-265, 1980.
Meghji, S., et al., Calcif. Tiss. Int., 36, 139-149, 1988.
Mundy, G.R., et al., J. Bio. Chem., 268, 10087-10094, 1993.
Bonewald, L. F., et al., J. Bone Miner. Res., 11, 1619-1627, 1996.
Bonewald, L.F. et al., J. Bone Miner. Res., 11, 521-529, 1996.
Gregg Wesolowski et al., Experimental Cell Research, 219, 679-686, 1995.
Eijiro Jimi, et al., Endocrinology, 137, p. 2187-2190, 1996.
Y. Wada, et al., Bone, 22, 479-485, 1998.
Sung-Eun Lee, "Design, Syntheses, and Evaluation of the Functional Molecules for the Treatment of the LTB4 related disease and electroluminescent device," Doctoral Dissertation, Department of Chemistry, Graduate School of Arts and Science, Busan Univ., South Korea, Aug. 1999.

*Primary Examiner* — Sreeni Padmanabhan
*Assistant Examiner* — Kendra D Carter
(74) *Attorney, Agent, or Firm* — Arent Fox LLP

(57) ABSTRACT

This invention relates to a pharmaceutical composition containing 4-[(4-thiazolyl)phenoxyl]alkoxy-benzamidine derivatives expressed by the following formula 1 for the prophylaxis and treatment of osteoporosis and more particularly, to the use of 4-{5-[4-(5-isoproply-2-methyl-1,3-thiazol-4-yl) phenoxyl]pentoxy}-benzamidine or N-hydroxy-4-{5-[4-(5-isopropyl-2-methyl-1,3-thiazol-4-yl)phenoxyl]pentoxy}-benzamidine expressed by the following formula 1 as a pharmaceutical composition for the prophylaxis and treatment of osteoporosis.

7 Claims, 12 Drawing Sheets

USE OF 4-[(4-THIAZOLYL)PHENOXY] ALKOXY-BENZAMIDINE DERIVATIVES FOR THE PROPHYLAXIS AND TREATMENT OF OSTEOPOROSIS

CROSS REFERENCE TO RELATED APPLICATIONS

This application is a continuation-in-part of U.S. patent application Ser. No. 10/484,094, filed Jan. 16, 2004 and claiming the benefit of priority to PCT/KR 2002/00463 filed Mar. 19, 2002 and KR 2001-43490 filed Jul. 19, 2001.

TECHNICAL FIELD

The present invention relates to a pharmaceutical composition containing 4-[(4-thiazolyl)-phenoxy]alkoxy-benzamidine derivatives represented by the following formula 1 for the prophylaxis and treatment of osteoporosis and more particularly, to the pharmaceutical composition containing 4-{5-[4-(5-isopropyl-2-methyl-1,3-thiazol-4-yl)phenoxy]pentoxy}-benzamidine (hereinafter referred to as "DW1352") or N-hydroxy-4-{5-[4-(5-isopropyl-2-methyl-1,3-thiazol-4-yl)phenoxy]pentoxy}-benzamidine (hereinafter referred to as "DW1350") represented by the following formula 1, for the prophylaxis and treatment of osteoporosis.

Formula 1

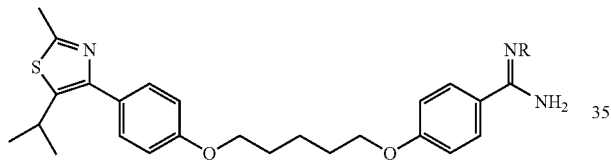

Wherein, R is a hydrogen atom or a hydroxy group.

BACKGROUND ART

Bone is the structural material of the body's framework and serves to maintain the necessary bone mass and structure. Bone contains calcium ($Ca^{2+}$) and plays an important role in maintaining the calcium level in the blood. To this end, the growth of bone is a metabolic balance between the activity of osteoblasts and osteoclasts in the bone remodelling cycle.

When the balance between bone absorption and bone formation is disrupted, the amount of bone tissue replaced by osteoblasts fails to match that absorbed by osteoclasts, thus leading to osteoporosis, a common condition causing loss of bone density or bone mass. This disease is frequently occurring in middle-aged or elderly women.

To date, the established strategy has been to produce drugs capable of the prophylaxis of bone loss by inhibiting osteoclastic bone absorption. Attempts to develop alternative therapies, such as $LTB_4$ receptor antagonist, have been made but their development towards an effective anti-osteoporotic agent has been unsuccessful due to insufficient inhibition on osteoclastic bone absorption. Therefore, there is an urgent need for new osteoporosis therapies aimed at suppressing osteoclastic bone absorption.

The natural product leukotriene-$B_4$ (hereinafter referred to as "$LTB_4$") is one of the arachidonate metabolites formed via the 5-lipoxygenase pathway [Ford-Hutchinson, A. W. et al., Nature (London), 286, 264-265, 1980].

Recent studies have focused on the influence of arachidonate metabolites on the bone tissue metabolism.

5-lipoxygenase metabolites produced from osteoblasts are found to stimulate bone absorption (Meghji, S. et. al., Calcif. Tiss. Int. 36, 139-149, 1988); the interstitial cells C433 obtained from a giant cell tumor are involved in producing 5-lipoxygenase metabolites to increase the counts and activity of osteoblasts (Mundy, G. R., J. Bio. Chem. 268, 10087-10094, 1993); the bone absorption function may be stimulated with the addition of synthetic $LTB_4$ during the cultivation process of bone tissue (Bonewald, L. F., J. Bone Miner. Res. 11, 521-529, 1996); and both in vitro and in vivo studies have demonstrated that $LTB_4$ induces the bone absorption via production of osteoclasts (Bonewald, L. F., J. Bone Miner. Res. 11, 1619-1627, 1996).

Currently, many studies have been under way with the conception that some compound showing an antagonistic action against $LTB_4$ receptors may affect embolic diseases of bone tissue.

The inventors have conducted intensive studies to identify a number of diverse-structure compounds useful as effective $LTB_4$ receptor antagonists, aimed at suppressing osteoclastic bone absorption or stimulating osteoblastic bone formation. As a result, it has been identified that the 3-amino-1,2-benzoisoxazole derivative represented by the following formula 2 is effective in the prophylaxis and treatment of osteoporosis, while exerting antagonistic action against $LTB_4$ receptors.

The inventors filed a patent application for such compound on Feb. 4, 1998 (KR 98-003138).

Formula 2

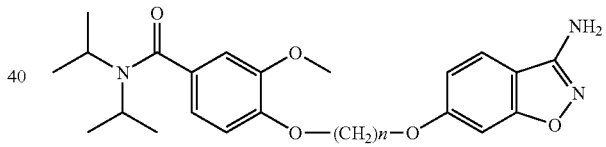

Wherein, n is an integer of 3-5.

In an effort to identify alternative osteoporosis therapies, the inventors have tested the inhibitory action of 4-[(4-thiazolyl)-phenoxy]alkoxy-benzamidine derivatives; among these derivatives, such compounds as 4-{5-[4-(5-isopropyl-2-methyl-1,3-thiazol-4-yl)phenoxy]pentoxy}-benzamidine or N-hydroxy-4-{5-[4-(5-isopropyl-2-methyl-1,3-thiazol-4-yl)phenoxyXpentoxy}-benzamidine are found to have significant effect in prophylacting bone loss by inhibiting osteoclastic bone absorption. Thus, the present invention has been finally completed.

DISCLOSURE OF THE INVENTION

The present invention relates to the therapeutic use of a pharmaceutical composition containing 4-{5-4-(5-isopropyl-2-methyl-1,3-tmazol-4-yl)phenoxy]pentoxy}-benzamidine or N-hydroxy-4-{5-[4-(5-isopropyl-2-methyl-1,3-thiazol-4-yl)phenoxy]pentoxy}-benzamidine represented by the following formula 1 for the prophylaxis and treatment of osteoporosis.

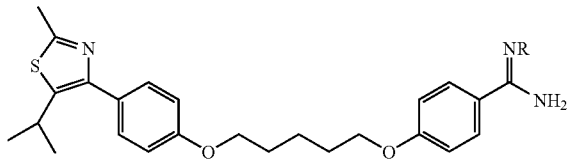

Formula 1

Wherein, R is a hydrogen atom or a hydroxy group.

4-[(4-thiazolyl)-phenoxy]alkoxy-benzamidine derivatives may be prepared by the conventional method (Lee Sung-eun, *Synthesis and Biological Activity of Natural Products and Designed New Hybrid Compounds for the Treatment of $LTB_4$ Related Disease*, Ph. D thesis, Graduate School of Pusan Univ., August 1999). Compounds of the present invention represented by the formula 1 may be also used with pharmaceutically acceptable salts using the following materials: inorganic acids (hydrochloric acid, bromic acid, sulfuric acid and phosphoric acid); organic acids (citric acid, acetic acid, lactic acid, tartaric acid, fumaric acid, formic acid, propionic acid, oxalic acid, trifluoroacetic acid, methanesulfonic acid, benzoic acid, maleic acid, gluconic acid, glycollic acid, succinic acid, 4-toluenesulfonic acid, galacturonic acid, embonic acid, glutamic acid or aspartic acid. According to the present invention, it is preferred to employ hydrochloric acid as inorganic acid and methanesulfonic acid as organic acid.

The anti-osteoporotic composition of the present invention may be applied in a therapeutically effective dose via various routes of administration. Any person having an ordinary knowledge in the technical field to which the present invention belongs can determine any dosage form and dosing regimen depending on purpose of administration, routes of administration, severity of diseases and body weight.

The anti-osteoporotic composition of the present invention contains 4-{5-[4-(5-isopropyl-2-methyl-1,3-thiazol-4-yl) phenoxy]pentoxy}-benzamidine or N-hydroxy-4-{5-[4-(5-isopropyl-2-methyl-1,3-thiazol-4-yl)phenoxy]pentoxy}-benzamidine represented by formula 1 and its pharmaceutically acceptable carriers.

The pharmaceutically acceptable carriers may include every type of standard pharmaceutical carriers used for the conventional dosage forms, such as sterile solution, tablet (including coated tablet) and capsules. The typical examples of such carrier include some excipients (e.g., starch, milk, sugar, specific clay, gelatin, stearic acid, talc, vegetable fat or oil, gum, glycols), or other conventional excipients. Such carriers may also include flavoring agents, color additives and other materials. The composition containing such carriers may be formulated by the conventional method.

The anti-osteoporotic composition of the present invention containing 4-{5-[4-(5-isopropyl-2-methyl-1,3-thiazol-4-yl) phenoxy]pentoxy}-benzamidine or N-hydroxy-4-{5-[4-(5-isopropyl-2-methyl-1,3-thiazol-4-yl)phenoxy]pentoxy}-benzamidine or its salts may be applied via the conventional routes of administration (e.g. oral, intravenous, intramuscular or transdermal) but is not limited to these routes of administration.

A wide range of therapeutic doses of 4-{5-[4-(5-isopropyl-2-methyl-1,3-thiazol-4-yl)phenoxy]pentoxy}-benzamidine or N-hydroxy-4-{5-[4-(5-isopropyl-2-methyl-1,3-thiazol-4-yl)phenoxy]pentoxy}-benzamidine has been established for the prophylaxis and treatment of osteoporosis. The therapeutic dose level for the treatment of osteoporosis is 10~1000 mg daily. Any person having an ordinary knowledge in the technical field to which the present invention belongs can determine the dose and dosing frequency depending on characteristics of the agent, severity of disease and body weight, size of inflammation and routes of administration.

In one specific embodiment of the present invention, the present inventors observed that there is not a direct correlation between $LTB_4$ receptor binding, on one hand, and the inhibition of osteoclast activity and/or enhancement of osteoblast activity, on the other hand.

The Compounds DW1350 and DW1352 only show a minor effect on $LTB_4$ receptor binding inhibition on human neutrophiles. However, these same compounds show an increased inhibition of osteoclast activity in comparison to other compounds. According to the Example 5, although DW1351 was a much better inhibitor of $LTB_4$ receptor binding than DW1350, the inhibition of osteoclast activity, differentiation or fusion, was much better for DW1350 than for DW1351. Although DW1351 was equal in $LTB_4$ receptor inhibition compared to DW1352, the latter was much better in osteoclast activity, differentiation or fusion or inhibition. Similarly, while DW1349 was much better in the inhibition of $LTB_4$ receptor binding than DW1350, DW1350 was much more effective in the inhibition of osteoclast activity, differentiation or fusion than DW1349. The same observation holds true for osteoblast activation mutatis mutandis.

The present inventors also assessed and compared the affect on osteoclast formation of DW1350 and four potent $LTB_4$ receptor antagonists, namely LY292728, SB209247, LY293111 and LY223982. According to the Example 6, the present inventors discovered that the four potent $LTB_4$ receptor antagonists, LY292728, SB209247, LY293111 and LY223982, did not affect the osteoclast formation in the absence of $LTB_4$, but did decrease the number of TRAP(+) MNCs in the presence of $LTB_4$. This means that, the antagonists are only functional in the presence of an agonist. In contrast, DW1350, on its own, affects osteoclast formation, regardless of the presence of $LTB_4$. This suggests that DW1350 does not belong in the same category as a typical $LTB_4$ receptor antagonist and might inhibit osteoclast formation through a feature unique to DW1350.

In another aspect, the invention provides a method for the prophylaxis of osteoporosis in a subject, the method comprising administering a composition comprising the compound of formula 1 or a salt thereof to the subject in an effective amount e to inhibit osteoclast activity and to stimulate osteoblast activity:

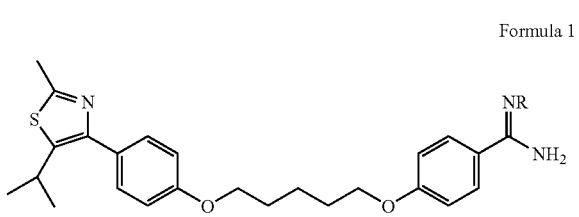

Formula 1

Wherein, R is a hydrogen atom or a hydroxy group.

As used herein, the term "prophylaxis" refers to all actions that inhibit or delay osteoporosis through the administration of composition.

In one embodiment, the invention provides a method for the prophylaxis of osteoporosis in a subject, the method comprising administering a composition comprising the compound of formula 1 or a salt thereof to the subject in an effective amount to inhibit osteoclast activity and to stimulate osteoblast activity, wherein in an in vitro Pit Formation Assay, said compound inhibits osteoclast activity.

In another embodiment, the invention provides a method for the prophylaxis of osteoporosis in a subject, the method comprising administering a composition comprising the compound of formula 1 or a salt thereof to the subject in an amount effective to inhibit osteoclast activity and to stimulate osteoblast activity, wherein in an in vitro Alkaline Phosphatase Assay, said compound stimulates osteoblast activity.

In yet another embodiment, the invention provides a method for the prophylaxis of osteoporosis in a subject, the method comprising administering a composition comprising the compound of formula 1 or a salt thereof to the subject in an amount effective to inhibit osteoclast activity and to stimulate osteoblast activity, wherein in an in vitro Cell Fusion Assay, said compound inhibits osteoclast activity.

In still another embodiment, the invention provides a method for the prophylaxis of osteoporosis in a subject, the method comprising administering a composition comprising the compound of formula 1 or a salt thereof to the subject in an amount effective to inhibit osteoclast activity and to stimulate osteoblast activity, wherein in an in vitro Tartarate Resistance Acid Phosphatase (TRAP) Staining Assay, said compound inhibits osteoclast activity.

In still another embodiment, the invention provides a method for the prophylaxis of osteoporosis in a subject, the method comprising administering a composition comprising the compound of formula 1 or a salt thereof to the subject in an amount effective to inhibit osteoclast activity and to stimulate osteoblast activity, wherein in an in vivo Assay, said compound inhibits the decrease of TBV (trabecular bone volume), Tbt (trabecular bone thickness), Tbn (trabecular bone number), Tbl (trabecular bone length) and Cbt (cortical bone thickness) induced by ovariectomy and the increase of Ocn (Osteoclast cell number) induced by ovariectomy.

In yet another embodiment, the invention provides a method for the prophylaxis of osteoporosis in a subject, the method comprising administering a composition comprising the compound of formula 1 or a salt thereof to the subject in an amount effective to inhibit osteoclast activity and to stimulate osteoblast activity, wherein in an in vivo Assay, said compound inhibits the decrease of TBV (trabecular bone volume) and Cbt (cortical bone thickness) induced by neurectomy.

In yet another embodiment, the invention provides a method for prophylaxis of osteoporosis in a subject, the method comprising administering a composition comprising the compound of formula 1 or a salt thereof to the subject in an amount effective to inhibit osteoclast activity and to stimulate osteoblast activity, wherein the compound is N-hydroxy-4-{5-[(4-(5-isopropyl-2-methyl-1,3-thiazol-4-yl)phenoxy]pentoxy}-benzamidine methane sulfonate or 4-{5-[4-(5-isopropyl-2-methyl-1,3-thiazol-4-yl)phenoxy]pentoxy}-benzamidine hydrochloride.

The immobilization osteoporosis model using sciatic nerve neurectomized ddY mice is useful for evaluation of anti-osteoporotic drugs, because several parameters are clearly decreased by neurectomy within 2 or 3 weeks after operation. In particular, for prophylaxis study, drug treatment is initiated immediately after neurectomy. According to the Example 7-1, the present inventors examined prophylactic effects of the compound in neurectomized ddY mice, and administration of the drug was initiated 2 days after neurectomy for prophylaxis study.

Estrogen-deficient ovariectomized osteoporosis model using ddY mice is also a useful for evaluation of anti-osteoporotic drugs, because several parameters are clearly decreased by ovariectomy within 4 to 6 weeks after operation. In particular, for prophylaxis study, drug treatment is initiated immediately after ovariectomy. According to the Example 7-2, the present inventors examined prophylactic effects of the compound in ovariectomized ddY mice, and administration of drug was initiated 3 days after ovariectomy for prophylaxis study.

From the results, the compounds of the present invention have more favorable effects in inhibiting the changes of various histomorphometric indices compared to that of Fosamax. In conclusion, it should be suggested that the compounds of the present invention have more favorable effects in the prophylaxis of osteoporosis superior to those of Fosamax.

BEST MODE FOR CARRYING OUT THE INVENTION

Figure 1:
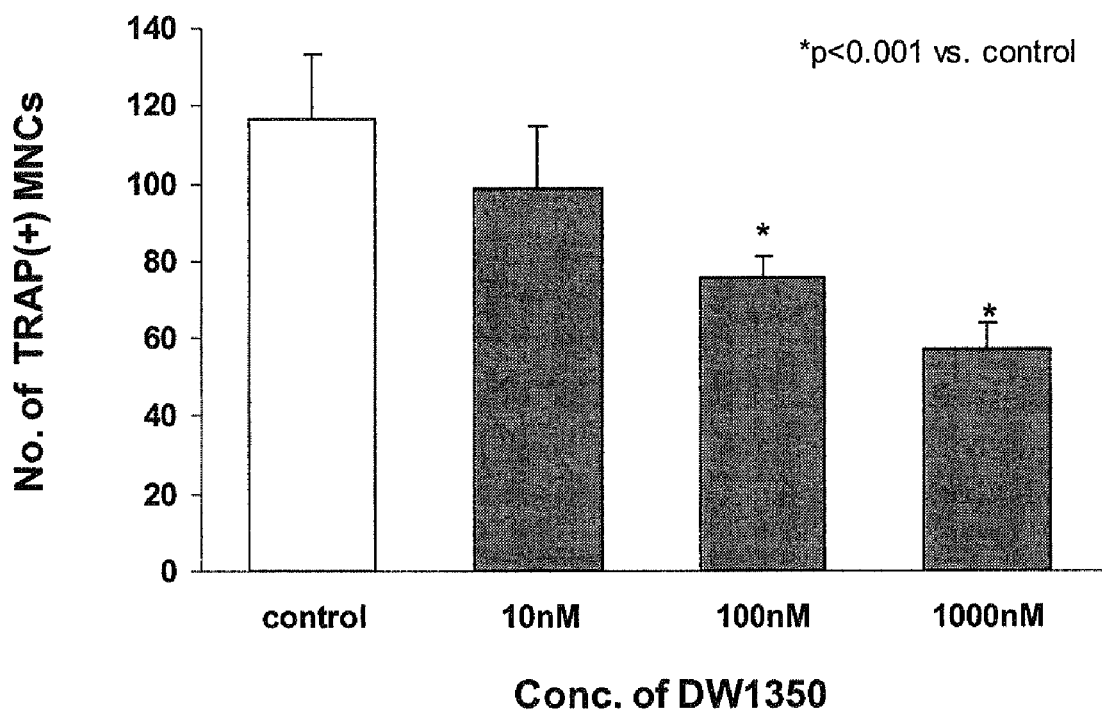
FIG. 1 shows the effect of DW1350 on TRAP(+) MNCs formation. Isolated rabbit osteoclasts containing suspension were plated on 60 mm culture dished under α-MEM with 2% FBS. After a 24 hr culture, DW1350 (10, 100 and 1000 nM) was added and treated for 48 hrs. The results are expressed as Mean±SD of the number of TRAP(+)MNCs ($n \geq 16$).

The present invention is explained in more detail by the following examples.

EXAMPLE 1

Inhibitory Effects on Osteoclast Differentiation of Each Test Substance

The effects of each test substance on osteoclast proliferation and differentiation process were evaluated via co-culture with osteoblast.

1. Preparation of Cells
 a) Preparation of Bone Marrow Cells

Tibia and Femora were aseptically ectomized from male ddY mice of 6-8 weeks to harvest bone marrow cells by using a syringe (21 G, Korea Green Cross).

The bone marrow cells were suspended in 5 mL α-MEM medium (Gibco BRL Co.) containing sodium bicarbonate (2.0 g/L), streptomycin (100 mg/L) and penicillin (100,000 unit/mL). The harvested cells were centrifuged at 800×g for 5 minutes to collect the whole quantity. To remove the red blood cells within bone marrow cells, 3 mL of Tris HCl (0.83% $NH_4Cl$, pH7.5) was added and well mixed. After centrifuging the above cells, the numbers of bone marrow cells were counted and then the bone marrow cells were immediately used for a co-culture system with osteoblast.

b) Preparation of Osteoblast

The calvaria were aseptically ectomized from neonate ICR mice of 1-2 days, washed with PBS solution and incubated with a mixture of enzyme solutions (0.2% collagenase and 0.1% dispase) at 37° C. gentle shaker. This procedure was sequentially repeated (10, 10, 10, 20, 20 and 20 minutes), and then the calvaria cells having the characteristics of osteoblast, were mostly released from III~VI digestion groups, were collected and washed with the medium (serum-free α-MEM). The washed cells were cultivated in α-MEM medium containing 10% FBS for 2-3 days. After subculturing, these cells were used for this experiment, and diluted to reach the concentration of $1 \times 10^6$ cells/mL for storage at −70° C.

2. Measurement of Osteoclast Differentiation
 a) Preparation of Specimen

N-hydroxy-4-{5-[4-(5-isopropyl-2-methyl-1,3-thiazol-4-yl)phenoxy]pentoxy}-benzamidine (DW1350) and 4-{5-[4-(5-isopropyl-2-methyl-1,3-thiazol-4-yl)phenoxy]pentoxy}-benzamidine (DW1352) used for the test substances of the present invention, and N,N-diisopropyl-4-[4-(3-aminobenzo[d]isooxazole-6-yloxy)butoxy]-3-methoxybenzamide (hereinafter referred to as "HS1141") and 4-[5-[4-(aminoiminomethyl)phenoxy]pentoxy]-3-methoxy-N,N-bis(1-methylethyl)benzamide maleic acid (Morrissey, M. M., Suh, H. U.S. Pat. No. 5,451,700; hereinafter referred to as "CGS-25019C"), $LTB_4$ receptor antagonists as control, were dissolved in a sterile distilled water to make desired concentrations following dilution. The volume of final specimen added to the medium was determined at the ratio of 1:1000.

b) Reaction with Specimens Via Co-Culture System

Bone marrow cells, so prepared from the above No. 1, and osteoblast from calvaria were co-cultured for osteoclast differentiation. Both bone marrow cells (25,000 cells/$cm^2$) and osteoblast (10,000 cells/$cm^2$) were plated on a 96 well plate in α-MEM medium containing 10% FBS with the specimen, and then the reaction mixture was cultured for 7 days. Some differentiation factors, such as dexamethasone ($10^{-6}$M) and vitamin $D_3$($10^{-9}$M), were also continuously added to the medium from the first day of cultivation. The media were changed with fresh media containing a mixture of specimens and differentiation factors every 2-3 day.

c) Evaluation of Osteoclast Differentiation

1) Preparation of Tartarate Resistance Acid Phosphatase (TRAP) Staining Solution TRAP was used as a marker to measure osteoclast in consideration of its characteristics showing a positive reaction to TRAP staining solution. TRAP staining solution was prepared in a manner such that 5 mg of naphtol AS-MS phosphate (sigma N-4875), a substrate and 25 mg of coloring agent (Fast Red Violet LB salt) were dissolved in N,N-dimethylformamide (about 0.5 mL) and with the addition of 0.1N $NaHCO_3$ buffer solution (50 mL) containing 50 mM of tartaric acid. The reaction mixture was stored in a refrigerator prior to use.

2) Staining Method

After a 7-day culture, the medium was removed from the wells and then the cells were washed once with PBS solution and fixed to PBS containing 10% formalin for 2-5 minutes. The cells were also fixed in a mixed solution, ethanol and acetone (1/1), for about 1 minute, and dried off. The cells were further treated by TRAP staining solution for 15 minutes and washed with PBS to measure the experimental results with the staining degree of cells under a microscopic examination.

3) Analysis on the Experimental Results.

The counts of osteoclast only with more than 3 nuclei showing the TRAP-positive reaction were calculated under a microscopic examination, and each test was reconfirmed over three times to insure more reliable data.

As shown in the following table 1, the inhibitory effect of each experimental group on the differentiation of osteoclast versus controls were expressed by inhibitory percentage value, and 50% inhibitory concentration on osteoclast differentiation was calculated as $IC_{50}$.

The anti-osteoporotic effect of each test substance were compared with controls, such as CGS-25019C and HS1141

(U.S. Pat. No. 6,150,390 and Korea Patent Application No. 98-3138), and a conventional anti-osteoporotic agent belonging to the same member of CGS-25019C, which demonstrates the antagonistic action to the existing LTB4 receptor.

TABLE 1

| Specimen | % inhibitory action | | | | |
|---|---|---|---|---|---|
| | 3.2 nM | 16 nM | 80 nM | 400 nM | $IC_{50}$ |
| DW1350 | 1.0 | 68.8 | 82.3 | 88.0 | 19.87 nM |
| DW1352 | 50.0 | 81.8 | 83.9 | 92.7 | 1.25 nM |
| HS1141 | 1.2 | 3.0 | 12.0 | 23.5 | — |
| CGS-25019C | −8.9 | 8.3 | 0.0 | 17.7 | — |

As shown in the table 1, the experimental results indicate that the inhibitory effect of both DW1350 and DW1352 against osteoclast proliferation and differentiation were significantly better than those of HS1141 and CGS-25019C. These test substances, which affect the osteoclast differentiation at a low concentration, may prove to be effective for the prophylaxis and treatment of osteoporosis.

EXAMPLE 2

Fusion Assay

This assay is designed to evaluate the influences of each test substance in terms of osteoclast fusion during the differentiation process in which immature prefusion osteoclasts (pOC; osteoclast structure with one more nuclei) were transformed into mature multinucleated osteoclast (OCL) via cell to cell fusion (Gregg Wesolowski et al. Experimental Cell Research 219,679-686, 1995).

1. Preparation of Prefusion Osteoclast (pOC)

The prefusion osteoclast can be obtained via co-culture of both bone marrow cells and osteoblast, as prepared from Example 1. The mixture of both osteoblast (about $5 \times 10^5$ cells/plate) and bone marrow cells (about $1 \times 10^7$ cells/plate) were co-cultured in a 100 mm culture dish. Some differentiation factors, such as dexamethasone ($10^{-6}$M) and vitamin D3 ($10^{-9}$M), were added to the medium from the first day of culture. The medium was changed with a fresh medium containing differentiation factors every 2 days.

Since a great number of the prefusion osteoclasts having one or more nuclei in fusion process were formed during 4-day co-culture, the cells were separated and co-cultivation after 4 days. The medium was removed from the cells and with the addition of 0.2% collagenase solution (4 mL), the cells were incubated at 37° C. for 20 mins to separate the attachment cells. Since the majority of separated cells were osteoblasts, all osteoblasts were washed with PBS solution two or three times for their complete removal.

After the remaining prefusion osteoclasts were separated via reaction for 20 mins with the addition of echistatin containing 10% BSA, the cells were harvested by centrifuge.

2. Reaction of Fusion Experiment

The test substances diluted at each concentration were diluted at the desired concentration in α-MEM medium (addition of 10% FBS) to load them into a 96-well microplate in a dose of 100 uL per well. The osteoclastic monocytes, so separated from the preceding No. 1, were plated on a 96-well microplate in a dose of $5 \times 10^3$ cell/100 uL per well and cultured at 37° C. for 24 hrs, thus successfully resulting in the osteoclast fusion. In the case of specimen-free and positive controls, experiments were performed in the same manner as above. The positive control use for this experiment includes 4-{4-[4-(5-isopropyl-2-methyl-1,3-thiazol-4-yl)phenoxy]butoxy}-benzamidine (hereinafter referred to as "DW1351") and N— hydroxy-4-{4-[4-(5-isopropyl-2-methyl-1,3-thiazol-4-yl)phenoxy]butoxy}-benzamidine (hereinafter referred to as "DW1349") which have a similar chemical structure to HS1141, CGS-25019C, DW1350 and DW1352.

3. Measurement of Osteoclast Fusion and its Analysis

The medium was removed from the cells and then the cells were washed once with PBS and fixed to a PBS solution containing 10% formalin for about 5 mins. The cells were again fixed to both ethanol and acetone (1/1) in a mixing solution for about 5 mins and dried off. The cells were further treated by TRAP staining solution for 15 mins and washed with water to observe the cells under the microscope. The TRAP-positive osteoclast counts, which were differentiated from monocyte to multinucleated cells (osteoclast having more than 10 nuclei) via fusion process, were measured.

The following table 2 shows the differences of measured cell counts versus control as % inhibitory concentration.

TABLE 2

| Specimen | Inhibitory action (%) | | | | |
|---|---|---|---|---|---|
| | 0.08 uM | 0.4 uM | 2 uM | 10 uM | $IC_{50}$ |
| DW1350 | 4.50 | 25.64 | 80.00 | 97.95 | 0.81 uM |
| DW1352 | 5.13 | 24.72 | 87.18 | 98.97 | 0.74 uM |
| HS1141 | 2.1 | 12.31 | 15.71 | 36.29 | — |
| CGS-25019C | 10.14 | 13.04 | 13.77 | 12.32 | — |
| DW1351 | 0.0 | 0.0 | 38 | 74 | — |
| DW1349 | 0.0 | 2.3 | 4.5 | 18 | — |

As shown in the table 2, the experimental results demonstrate that both DW1350 and DW1352 exerted significant inhibitory effects against osteoclast fusion ($IC_{50}$: 0.81 and 0.74 uM, respectively). More specifically, the inhibitory effects of both DW1350 and DW1352 against osteoclast fusion make it possible to prevent mature osteoclast formation which will result in significant inhibition of osteoclast-dependent bone absorption. The control CGS-25019C showed little inhibitory effect against osteoclast fusion, irrespective of drug concentrations. The inhibitory effect of HS1141 against osteoclast fusion was lower than those of DW1350 and DW1352, although the former was dependent on drug concentrations. In the case of DW1349 and DW1351 having extremely similar structure to DW1350 and DW1352, their inhibitory effects against osteoclast fusion were significantly lower than DW1350 and DW1352, although the former was dependent on drug concentrations like HS1141.

Therefore, it is expected that among 4-[(4-thiazolyl)phenoxy]alkoxy-benzamidine derivatives, both DW1350 and DW1352 may be developed as new anti-osteoporotic agents by effectively inhibiting mature osteoclast formation based on the inhibitory mechanism of osteoclast fusion.

EXAMPLE 3

Measurement of Bone Resorption

Pit Formation Assay

The mature osteoclast (OCL) is mainly involved in removing mineral by bone resorption. This experiment is designed to measure the inhibitory effects of each test substance on the bone resorption of osteoclast using ivory fragment (Eijiro Jimi et al. Endocrinology 137, p 2187-2190, 1996).

1. Preparation of Mature Osteoclast a) Preparation of Collagen Gel Solution

The co-culture system for both bone marrow cells and osteoblast was performed using a cultivation dish containing collagen gel (cell matrix Type I-A). Collagen, 5-fold concentrated α-MEM medium and 0.05M NaOH buffer solution (2.2% $NaHCO_3$, pH7.4) were mixed at the ratio of 7:2:1 at a low temperature, and then storage at a low temperature. Then, 4 mL of the mixed solution was added to a 100 mm culture dish, applied evenly and left at 37° C. for 5 minutes.

b) Preparation of Mature Osteoclast Via Co-Culture System

Using α-MEM medium, the mixture of both bone marrow cells (about $1\times10^7$ cells/plate) and osteoblast (about $5\times10^5$ cells/plate), so separated from Example 1, were plated on a 100 mm dish containing collagen gel. The co-culture was performed in the presence of differentiation factors such as vitamin D ($10^{-9}$M) and dexamethasone ($10^{-6}$M). As described above, a great number of mature multinucleated osteoclasts with the ability of bone resorption were obtained via a 7-day co-culture. The medium was removed from the cells and with the addition of 0.2% collagenase solution, the attachment cells were separated by incubation for 20 minutes. The cells were collected via centrifuge. The harvested crude osteoclasts were again diluted in α-MEM medium to make the cells of 5,000 cells/100 ul.

2. Preparation of Hematoxylin Staining Solution

Hematoxylin staining solution was prepared in a manner such that hematoxylin (1 g) was dissolved in 500 ml of distilled water and was added to 500 ml of distilled water and sodium iodide (0.2 g). The reaction mixture was stirred for 15 mins. Ammonium alum (50 g) and 7.5 ml of acetic acid were further added to the reaction mixture and filtered off.

3. Reaction on Ivory Fragment

After the ivory fragments, cut to a thickness of 1 mm, were sterilized, each fragment was placed into a 96 well plate, and 100 ul α-MEM medium (10% FBS) was added. To measure its inhibitory effect against the pit formation of osteoclast, each test substance was added in a maximum amount of 3 ul per concentration.

With the addition of test substances, 100 ul of osteoclast solution was further added, mixed vigorously and cultured using a 5% $CO_2$ incubator at 37° C. for 24 hrs. To observe the pits formed on the ivory fragments, the portion of grown osteoclast was directed upward and placed on a paper towel after removing from the 96 well plate. With the removal of cells on the ivory, 10 ul of hematoxylin solution was dropped on the ivory to perform the staining for about 5 minutes. The surface of the ivory fragments was rubbed with a soft cotton pole to completely remove the staining solution.

4. Observation of Pits Formation and its Analysis

The following table 3 shows the number of pits on ivory fragment versus control as an inhibition percentage at various concentrations under a microscopic examination.

TABLE 3

| Specimen | Inhibitory action (%) | | | | | |
|---|---|---|---|---|---|---|
| | 0.016 μM | 0.08 μM | 0.4 μM | 2 μM | 10 μM | $IC_{50}$ |
| DW1350 | 32.2 | 53.9 | 65.2 | 84.3 | 91.3 | 0.075 uM |
| DW1352 | 25.0 | 48.7 | 61.3 | 81.7 | 90.0 | 0.131 uM |
| HS1141 | 9 | 33 | 50.4 | 75.3 | 88.7 | 0.421 uM |
| CGS-25019C | 0 | 0 | 2 | 9.2 | 17.3 | — |

As shown in the table 3, the experimental results demonstrate that both DW1350 and DW1352 exerted significant inhibitory effect against the bone resorption of osteoclast. It also reveals that DW1350 and DW1352 had the $IC_{50}$ values of 0.075 uM and 0.131 uM, respectively, 3-6 times of inhibitory effect higher than HS1141. In the case of CGS-25019C, a positive control, it had a low inhibitory effect against the osteoclastic bone resorption.

EXAMPLE 4

Evaluation of Alkaline Phosphatase (ALP) Activity to Measure Osteoblast Activity This experiment is designed to evaluate the differentiation and activity of osteoblast via ALP activity having a close relationship with osteoblastic bone formation (Y. Wada et al., Bone, 22,479-485, 1998).

MC3T3-E1 cells (3,000 cells/well) derived from osteoblast were placed on a 96 well plate and after 24-hour culture the media were changed with fresh medium containing various differentiation factors such as ascorbic acid (100 ug/ml) and β-glycerophosphatic acid (5 mM). The medium was also treated with test substances and the medium, containing differentiation factors and the specimen, was changed with a fresh medium every 3 days.

The culture was terminated after two weeks to measure ALP activity. With the removal of the supernatant, 0.5% Triton X-100 were added for the lysis of cells. 100 ul of p-nitrophenylphosphate (1.21 mM) was added to 50 ul of above mixture. The mixture was incubated at 37° C. for 30 mins and with the addition of 0.2N sodium hydroxide (50 ul), the reaction was terminated. The standard curve was indicated at the absorbance of 405 nm using p-nitrophenol as a standard material and then the absorbance of test substances, so reacted, was measured to observe the production amount of p-nitrophenol.

As shown in the following table 4, the units of ALP activity were determined as the amount of p-nitrophenol (nM) produced per time (per min or hour)/1 ug protein after measuring the amounts of protein contained in the reaction mixture of each test substance.

TABLE 4

| Specimen ($10^{-8}$M) | ALP activity (units) |
|---|---|
| DW1350 | 19.8 |
| DW1352 | 17.1 |
| HS1141 | 15.2 |
| CGS-25019C | 15.0 |
| Controls | 13.5 |

As shown in the table 4, the experimental results demonstrate that DW1350 exerted the highest ALP activity among all test substances. The ALP activities of DW1352 were also found to be superior to those of controls HS1141 and CGS-25019C. This experiment has indicated that both DW1350 and DW1352 were effective in stimulating osteoblast activity by affecting osteblast differentiation and formation. Therefore, both DW1350 and DW1352 are quite useful drugs for the prophylaxis and treatment of osteoporosis, since the can suppress osteoclastic function, while stimulating osteoblastic activity.

EXAMPLE 5

$LTB_4$ Receptor Binding Assay, and Measurement of Osteoclast Differentiation and Osteoblast Activity The following describes studies to show that there is not a direct correlation between the $LTB_4$ receptor antagonist activity of DW 1350 and several other structurally related compounds described in the Lee Dissertation, e.g., DW1349, DW1351 and DW1352, and the ability of the compounds to inhibit osteoclast activity and/or enhance osteoblast activity.

1. The $LTB_4$ Receptor Binding Assay a) Materials and Method

Neutrophils (PMN) were purified from freshly drawn human blood by standard techniques or dextran T-500 sedimentation and centrifugation on Ficoll/Paque (pharmacia) followed by hypotonic lysis of erythrocyte. The purified PMN were resuspended to a final concentration of $3 \times 10^7$ cells/ml in HESS (Hank's balanced salt solution, Gibco).

The assay was performed following the method described elsewhere (Brown. A. R.; Greenham, N. C.; Burroughes, J. H.: Bradely, D. C. C.; Friend. R. H.; Burn, P. L.; Kraft. A.: Holmes, A. B.; *Chem. Phys, Lett.* 1992, 200, 1246). $LTB_4$ receptor binding assay was performed in $12 \times 75$ mm polypropylene tubes containing 0.5 nM of $[^3H]$-$LTB_4$ (200 Ci/mmol), competitive compound, and cells suspended in HBSS ($3 \times 10^6$ cells) (final volume: 200 ul). The tubes were incubated on ice for 45 minutes. Free and PMN bound $[^3H]$-$LTB_4$ were separated by filtration through Whatman GF/C filters. The filters were then washed three times with 5 ml of ice cold Tris buffer (pH 7.4). The filter were air-dried and placed into scintillation vials. The radioactivity was measured by liquid scintillation spectrometry. The specific binding was determined as the count difference total binding and binding in the presence of 1000-fold excess of unlabeled $LTB_4$ ($S_{control}$). The $LTB_4$ binding activity was calculated from the percent inhibition of specific $[^3H]$-$LTB_4$ binding at various concentrations ($S_{sample}$).

Calculation of percent inhibition(%)=$(Sc-Ss)/Sc \times 100$

Sc: specific binding of control

Ss: specific binding of sample b) Results and Discussion

The following results were presented in the Lee Dissertation.

TABLE 5

Inhibition of $LTB_4$ receptor Binding to the human Neutrophile.

| Cpd No. | HS# | R | n | Inhibition (%) | | | $IC_{50}$ (nM) |
|---|---|---|---|---|---|---|---|
| | | | | 10 nM | 100 nM | 1 uM | |
| 54a | 1351 | $C(NH_2)$=$NH \cdot HCl$ | 2 | — | 89 | 100 | |
| 54b | 1352 | $C(NH_2)$=$NH \cdot HCl$ | 3 | — | 88 | 100 | |
| 53a | 1349 | $C(NH_2)$=$NH$—$OH$ | 2 | — | 32.7 | 87.2 | |
| 53b | 1350 | $C(NH_2)$=$NH$—$OH$ | 3 | — | <10 | 92.3 | |

TABLE 6

Inhibition of $LTB_4$ receptor Binding to the human Neutrophile*

| Cpd No. | # | R | n | Inhibition (%) | | | $IC_{50}$ (nM) |
|---|---|---|---|---|---|---|---|
| | | | | 10 nM | 100 nM | 1 uM | |
| CGS-25019C | | $C(NH_2)$=$NH \cdot HCl$ | 3 | 25 | 84 | 99 | 41.2 |

TABLE 7

Inhibition of $LTB_4$ receptor Binding to the human Neutrophile*

| Cpd No. | HS# | n | Inhibition (%) | | | $IC_{50}$ (nM) |
|---|---|---|---|---|---|---|
| | | | 10 nM | 100 nM | 1 uM | |
| 54a | 1141 | 2 | 64 | 95 | 100 | 7.0 |

At a concentration of 100 nM, HS1141 of Table 7 showed 95% inhibition which is the strongest inhibition among the test compounds. CGS25019c of Table 6 showed 84% inhibition, and DW1351 and DW1352 of Table 5, 89% and 88% inhibition respectively. However, DW1349 inhibited the $LTB_4$ receptor binding by 32.7% and DW1350 by 10%, showing the weakest inhibition. DW1349 showed more than three times the inhibition of DW1350, while the structure of these compounds was very similar, being different in only one carbon. DW1351, which has an amidine, showed more than eight times the inhibition of DW1350, which has N-hydroxyamidine in the structure.

2. The Inhibitory Effect on Osteoclast Differentiation by the Compounds a) Materials and Method Method of evaluating the effects of the compounds on osteoclast differentiation:

To investigate the effect of compounds on osteoclast differentiation, co-culture between bone marrow cells ($2.5 \times 10^5$ cells/cm$^2$) and calvaria-derived osteoblastic cells ($4 \times 10^4$ cells/cm$^2$) was conducted in the presence of $1.25(OH)_2D_3$ ($10^{-8}$ M) and dexamethasone ($10^{-7}$ M) with $\alpha$-MEM containing 10% FBS (referred as "osteoclastic medium"). Bone marrow cells were isolated from the femora of 6-week-old ddY mice and primary osteoblastic cells were isolated from the calvariae of newborn ICR mice by sequential digestion with 0.2% collagenase. The medium was changed every two days with fresh osteoclastic medium. An index of osteoclast formation was determined by counting TRAP-positive multinucleated osteoclasts (TRAP(+)MNCs). On day 6, the cells were fixed with 10% formaldehyde and stained for TRAP. The number of TRAP(+) MNCs containing more than 6-7 nuclei was counted under a microscope (ZEISS Axiovert 25, Switzerland). The results are shown as the relative inhibitory activity (% inhibition) compared to the control group.

b) Results and Discussion

TABLE 8

| Specimen | % inhibitory action | | |
|---|---|---|---|
| | 0.01 uM | 0.1 uM | 1 uM |
| DW1349 | 31.9 | 46.8 | 85.5 |
| DW1350 | 38.5 | 62.7 | 88.7 |
| DW1351 | 23.0 | 30.6 | 61.5 |
| DW1352 | 27.1 | 41.3 | 80.9 |
| HS1141 | 11.4 | 36.4 | 72.9 |
| CGS-25019C | 11.2 | 29.5 | 36.9 |

(1) Comparison Between DW1349 and DW1350:

While (at the concentration of 0.1 uM in table 5) DW1349 (32.7%) showed at least three times more inhibition than DW1350 (<10%) on the $LTB_4$ receptor binding, DW1350 exerted 1.34 times more inhibition of osteoclast differentiation than DW1349, as shown in Table 8.

(2) Comparison Between DW1351 and DW1352:

DW1351 (89%) and DW1352 (88%) showed similar $LTB_4$ receptor binding inhibition at 0.1 uM concentration in Table 5. However, in the inhibition of the osteoclast differentiation, DW1352 was stronger than DW1351 by about 1.35 times.

(3) Comparison Between DW1351 and DW1350:

DW1351 was a much better inhibitor of the $LTB_4$ receptor binding than DW1350, as shown in Table 5 (eight times better at 0.1 uM). However, as shown in Table 8, in the inhibition of the osteoclast differentiation, DW1350 was about two times better than DW1351.

3. The Inhibitory Effect of the Compounds on Osteoclast Fusion a) Materials and Method The effect of the compounds on the fusion of osteoclasts was examined using purified prefusion osteoclasts (pOC, mononuclear and binuclear osteoclasts). Co-cultures of bone marrow cells ($2 \times 10^7$ cells/dish) and newborn mice calvariae ($1 \times 10^6$ cells/dish) were maintained in 100-mm-diameter dishes for 4 days with osteoclast differontiarion factor. Cultures were washed twice with PBS and treated with 0.1% collagenase/dispase at 37° C. for 20 minutes. Released cells, mostly osteoblasts, were removed with a pipet and the plates were washed three times with PBS. The remaining cells were incubated with 30 uM echistatin in α-MEM containing 1% BSA for 20 min at 37° C. These cells were collected, pelleted, and washed once with α-MEM containing 10% FBS. The cells released by this treatment were the subject of the fusion assay. More than 90% of the cells in the pOCs preparation used in the present study were positive for TRAP.

pOCs (15,000 cells/well) were plated on 96 well culture plates with or without various compounds. After culture for 18 hours, the cells were fixed and stained for TRAP. The number of TRAP-positive MNCs with more than 10 nuclei was counted as pOC-derived OCLs and the results were shown as an inhibitory activity (% inhibition) compared to control group.

b) Results and Discussion

TABLE 9

Fusion assay

| Specimen | Inhibitory action (%) | | | | $IC_{50}$ |
| --- | --- | --- | --- | --- | --- |
| | 0.08 uM | 0.4 uM | 2 uM | 10 uM | |
| DW1349 | 0.0 | 2.3 | 4.5 | 18 | — |
| DW1350 | 4.50 | 25.64 | 80.00 | 97.95 | 0.81 uM |
| DW1351 | 0.0 | 0.0 | 38 | 74 | — |
| DW1352 | 5.13 | 24.72 | 87.18 | 98.97 | 0.74 uM |
| HS1141 | 2.1 | 12.31 | 15.71 | 36.29 | — |
| CGS-25019C | 10.14 | 13.04 | 13.77 | 12.32 | — |

The following observations regarding the effects of the compounds may be made:

(1) Comparison Between DW1349 and DW1350:

At a concentration of 2 uM, DW1350 showed 17.8 times stronger inhibition of osteoclast fusion than DW1349, even though DW1349 was a better inhibitor of the $LTB_4$ receptor binding (at 100 nM, Table 5)

(2) Comparison Between DW1351 and DW1352

DW1352 showed 2.3 times more inhibition than DW1351, while the $LTB_4$ receptor binding inhibition was similar for these two compounds (at 100 nM, Table 5)

(3) Comparison Between DW1351 and DW1350

Contrary to the $LTB_4$ receptor binding inhibition (at 100 nM, Table 5), DW1350 was a two fold better inhibitor of osteoclast fusion than DW-1351.

4. The Inhibitory Effect on Osteoclast Differentiation by the Compounds a) Materials and Method Method for evaluating the effects of the compounds on osteoclast activity: Multinucleated osteoclasts were developed on collagen gel plates by co-culture system as described. On day 6-8 of the co-culture, multinucleated OCLs were detached from plates by 0.2% collagenase treatment ("crude OCLs"). Crude OCLs suspended in α-MEM containing 10% FBS were placed on a dentine slice (4 mm diameter) in a 96-well culture plate. After 2 h of preincubation, the dentine slice was transferred to another plate containing natural compounds (1 ug/ml) and vehicle and incubated for 24 h more. At the end of the incubation, cells were removed by 1 M $NH_4OH$ treatment and resorption pits formed (in the slices stained with Mayer's hematoxylin). Resorption pits were enumerated with an image analyzer and compared to the control group. The results were showed as the relative inhibitory activity (% inhibition)

b) Results and Discussion

TABLE 10

Measurement of bone resorption (pit formation assay)

| Specimen | Inhibitory activity (%) | | |
| --- | --- | --- | --- |
| | 0.01 uM | 0.1 uM | 1 uM |
| DW1349 | 19.3 | 36.1 | 64.7 |
| DW1350 | 45.2 | 52.6 | 72.6 |
| DW1351 | 2.1 | 26.7 | 51.8 |
| DW1352 | 21.7 | 36.0 | 64.1 |
| HS1141 | 8.2 | 22.7 | 52.7 |
| CGS-25019C | 0(−24) | 10.4 | 24.8 |

The following observations may be made regarding the ability of the compounds to inhibit osteoclast activity:

(1) Comparison Between DW1349 and DW1350:

While DW1349 was superior than DW1350 in $LTB_4$ receptor binding inhibition, in inhibiting osteoclast activity DW1350 was about 1.45 times better than DW1349.

(2) Comparison Between DW-1351 and DW1352:

While the $LTB_4$ receptor binding inhibition of DW1351 and DW1352 were similar, DW1352 showed about 1.35 times more inhibition of osteoclast activity than DW1351 in Table 10.

(3) Comparison Between DW1351 and DW1350:

Contrary to $LTB_4$ receptor binding inhibition, DW1350 was a two-fold better inhibitor of ocsteoclast activity than DW1351 in Table 10.

5. The Ability of the Compounds to Enhance Osteoblast Activity a) Materials and Method Primary osteoblastic cells isolated from the calvariae of newborn ICR mice were grown to confluence in α-MEM containing 10% FBS. These cells were plated at a density of $1 \times 10^5$/ml in tissue culture dishes. After 24 h, cells were changed with a differentiation medium containing ascorbic acid (50 ug/ml) and β-glycerophosphate (10 mM) with or without the compounds and further cultured for 3 days. Cells were washed twice with PBS and harvested. For the measurement of ALP activity and total protein content, cells were extracted into 0.1% Triton X-100 in PBS containing 1 mM $MgCl_2$ and centrifuged at 1.000×g for 5 minutes. Enzyme activity was determined in supernatants by colorimetric procedure using p-nitrophenyl phosphate (PNP) as a substrate at a wavelength of 405 nm and the protein content was determined by a Bio-Rad protein assay kit. The ALP unit was expressed as nmol PNP/ug protein/min. The results were showed as ALP unit and % activation compared to control group.

b) Results and Discussion

TABLE 11

Evaluation of alkaline phosphatase(ALP) activity to measure osteoblast activity

| Specimen | ALP activity (Unit (% of control)) | |
|---|---|---|
| | 0.01 uM | 0.1 uM |
| DW1349 | 19.0(113.2) | 17.2(101.6) |
| DW1350 | 24.4(141.9) | 26.7(153.7) |
| DW1351 | 20.8(122.5) | 21.0(121.2) |
| DW1352 | 19.2(113.0) | 19.1(111.7) |
| HS1141 | 19.9(117.3) | 21.0(120.9) |
| CGS-25019C | 20.6(121.3) | 19.7(115.3) |
| Control | 16.8(100) | |

The following observations may be made regarding the ability of the compounds:

(1) Comparison Between DW1349 and DW1350:

While DW1349 is a better inhibitor of the $LTB_4$ receptor binding than DW1350, DW1350 was a 1.25 times better stimulator than DW1349 of osteoblast activity (measured by stimulator of ALP activity).

(2) Comparison Between DW1351, DW1352 and DW1350:

While DW1350 showed the lowest $LTB_4$ receptor binding inhibition among these compounds, DW1350 was the stimulation of osteoblast activity (ALP activity) by 1.15~1.25 times greater than DW1351 and DW1352.

EXAMPLE 6

Inhibitory Effects on Osteoclast Differentiation of DW1350 and $LTB_4$ Receptor Antagonists We carried out studies to show that there is not a direct correlation between the $LTB_4$ receptor antagonist activity of DW1350 and the ability of this compound to inhibit osteoclast activity and enhance osteoblast activity.

1. Materials and Method a) Isolation of Rabbit Osteoclasts

Rabbit osteoclasts were isolated as described by Victoria Tai's report (Doctoral Dissertation, 1997, Graduate Department of Pharmacology, University of Toronto) and Rraser P. Coxon et al. (*Methods in Molecular Medicine*, vol 80). Neonatal rabbits (New Zealand White) were sacrificed by ether-inhaling method under a hood. The removed long bones were dissected free of attached soft tissues and placed into ice-cold PBS. The long bones were cut longitudinally and mechanically curetted in 10 ml medium 199 with antibiotics (10 ug/ml penicillin G and 50 ug/ml gentamycin) in a glass Petri dish. Each bone was curetted with a scalpel blade and was finely minced. The fragments were then vigorously agitated by pipetting up and down using a pasteur pipette and vortex-mixed for 30 seconds. The fragments were allowed to settle and the cell suspension was then transferred to a 50 ml tube and the previous step repeated three times to a total volume of 40 ml. The bone fragments were allowed to settle (>1 min). The cell suspension was then transferred to a new 50 ml tube, passed through a 40 um cell strainer and centrifuged at 200 g for 8 minutes. The supernatant was removed and the pellet was immediately resuspended in α-MEM with 2% FBS (bicarbonate buffered medium).

b) Culture Condition for Compound Treatment 40 uL droplets of osteoclast-containing suspensions were plated onto 60 mm tissue culture plastic dishes or on dentine slices in 96-well microtiter plates in 2% medium. The cells were allowed ninety minutes for attachment before the addition of 2 mL α-MEM with 2% FBS. After 24 hr culture, cells were washed to remove non-adherent cells and replaced with fresh medium as describes below.

There were three experimental groups:

1) Single Treatment

After 24 hr in culture, the medium was replaced with fresh medium containing control, $LTB_4$ receptor antagonists (1000 nM), DW1350 (10, 100 and 1000 nM) or $LTB_4$ (100 nM) and the cultures were continued for an additional 48 hrs.

2) Simultaneous Treatment (Co-treatment)

After 24 hr in culture, the medium was removed and replaced with fresh medium containing both $LTB_4$ receptor antagonist (1000 nM) and $LTB_4$ (100 nM) or both DW1350 (1000 nM) and $LTB_4$ (100 nM). The cultures were continued for an additional 48 hrs.

3) Pre-treatment

After 6 hrs in culture, the medium was removed and cells were pretreated with $LTB_4$ receptor antagonists such as LY292728 (*Journal of Medical Chemistry*, 1995, vol. 38, No. 10, p 4411-4432), SB209247 (*Journal of Medical Chemistry*, 1996, vol. 39, No. 19, p 3837-3841), LY293111(*Journal of Medical Chemistry*, 1995, vol. 38, No. 10, p 4411-4432) and LY223982 (*Journal of Medical Chemistry*, 1993, vol. 36, p 3333-3340) or DW1350-containing medium and culture continued for 18 hrs. The medium was replaced with medium containing both $LTB_4$ receptor antagonist and $LTB_4$ or DW1350 and $LTB_4$. The cultures were continued for an additional 48 hrs.

All cells were cultured at 37° C. in a humidified atmosphere of 95% air and 5% $CO_2$ in bicarbonate buffered medium at pH 7.4.

Differentiated osteoclasts are multinucleated cells and have specific enzyme activity, such as 'tartrate-resistant acid phosphatase (TRAP)'. Therefore, Osteoclast formation was determined by counting the number of TRAP-positive multinucleated cells (TRAP(+) MNCs).

c) TRAP Staining & Statistical Analysis

After culture, the cells were fixed with 10% neutral buffered formalin for 30 min at 4° C., washed twice in distilled water and stained for TRAP activity by incubating with substrate. The number of TRAP(+)MNC with more than 2 nuclei was counted under photomicroscope.

Results were expressed as mean number of TRAP(+) MNC±SD of All experiments were done at least twice. Statistical analysis was performed for each experiment by student t-test.

d) $LTB_4$ Receptor Antagonist

To compare the effect between DW1350 and $LTB_4$ receptor antagonists on osteoclast formation, we employed four specific $LTB_4$ receptor antagonists, LY292728 ($K_i$ of 0.5 nM), SB209247 ($K_i$ of 0.8 nM), LY293111 ($K_i$ of 25 nM) and LY223982 ($IC_{50}$ of 13 nM). These potent antagonists could block the biological activity of $LTB_4$ with the specificity for its receptor.

2. Results and Discussion a) The Effect of DW1350 and $LTB_4$ Receptor Antagonist on the Formation of TRAP(+) MNC: Single Treatment without $LTB_4$.

Figure 2:
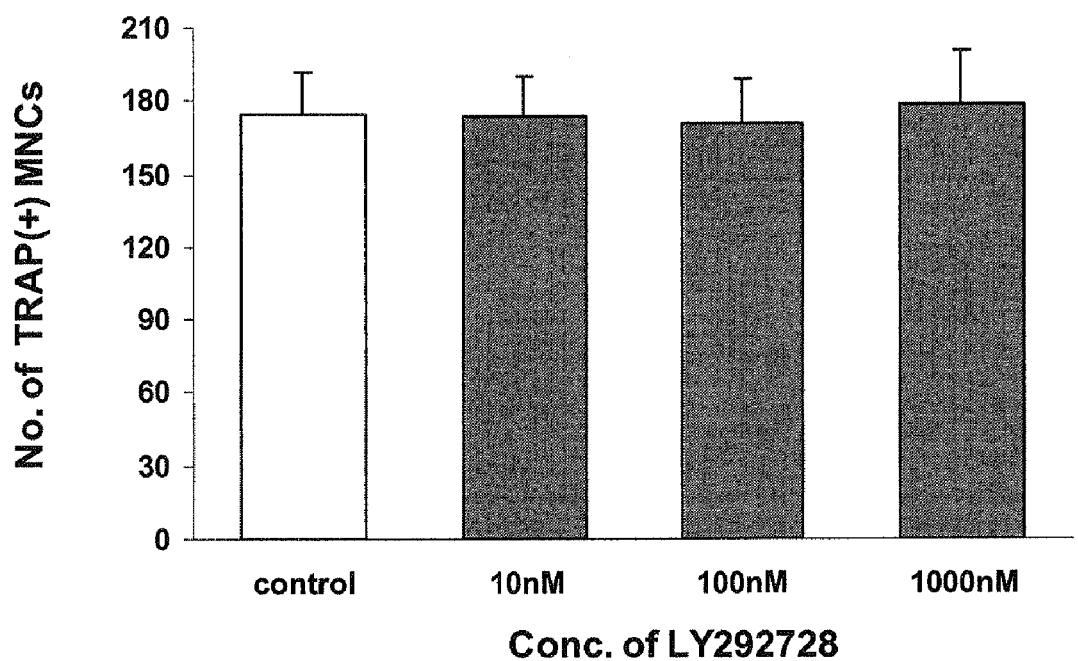
FIG. 2 shows the effect of LY292728 on TRAP(+) MNCs formation. An isolated rabbit osteoclasts containing suspension was plated on a 60 mm culture dish under α-MEM with 2% FBS. After 24 hours of culture, LY292728 (10, 100 and 1000 nM) was added and treated for 48 hrs. The results are expressed as Mean±SD of the number of TRAP(+)MNCs ($n \geq 6$).

We first investigated the effect of DW1350 on osteoclast formation in rabbit osteoclast-containing cultures on tissue culture ware. As shown in FIG. 1, the treatment with 10~1000 nM of DW1350 for 48 hours significantly decreased the number of TRAP(+) MNCs in a dose-dependent manner. No cytotoxic effect based on cell morphology was not observed. To confirm the effect of $LTB_4$ receptor antagonist on osteoclast formation by a single treatment, LY292728 was added into isolated rabbit osteoclast cultures for 48 hours. The result shown in FIG. 2 illustrated that the treatment with 10~1000 nM of antagonist had no significant effect on the number of osteoclasts. When osteoclasts were plated on dentin slices under the same culture conditions, we also observed a similar tendency of osteoclast formation on tissue culture plate.

Figure 3:
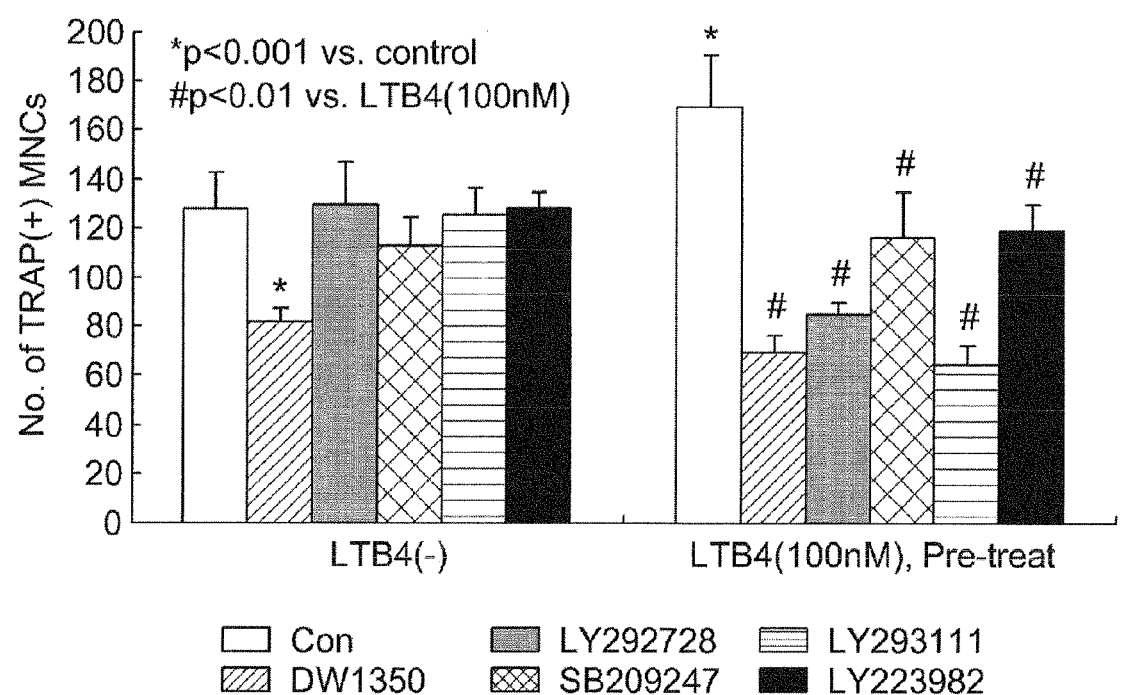
FIG. 3 shows the effect of $LTB_4$ receptor antagonists on TRAP(+)MNCs formation. An isolated rabbit osteoclasts containing suspension was plated on dentine slices under α-MEM with 2% FBS. After 24 hours of culture, DW1350, LY292728, SB209247, LY293111 and LY223982 at 1000 nM were added and treated for 48 hrs. The results are expressed as Mean±SD of the number of TRAP(+)MNCs ($n \geq 6$).

The compounds, including $LTB_4$ receptor antagonist and DW1350, at 1000 nM were treated in the culture (FIG. 3). The antagonists had no effect on the number of TRAP(+) MNCs, however DW1350 had a significant inhibition on the formation of osteoclasts.

From these results, we suggested that DW1350 by itself effects osteoclast formation but the other $LTB_4$ antagonists by themselves did not have an affect osteoclast formation.

b) The Effect of DW1350 and $LTB_4$ Receptor Antagonist on $LTB_4$-Induced Osteoclast Formation: Pre-Treatment & Combined Treatment with $LTB_4$.

We examined the effect of antagonists on the formation of rabbit osteoclasts under $LTB_4$-treated culture condition on dentin slices (FIG. 4-8). When 100 nM $LTB_4$ was treated in the culture for 48 hours there was a significant increase in the number of TRAP-positive osteoclasts compared to the control group with 30~40% increase.

Figure 4:
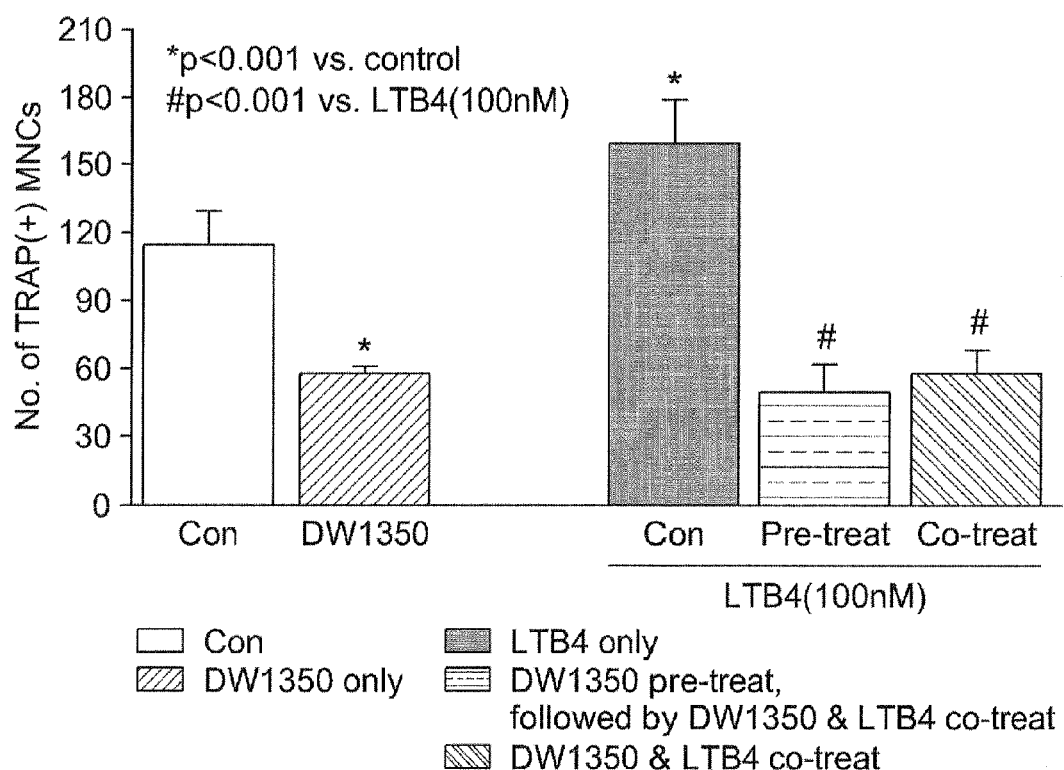
FIG. 4 shows the effect of DW1350 in $LTB_4$-induced Osteoclast formation. An osteoclast containing cell suspension was plated on dentin slices. Three treatment regimens as described in A-2 part were used. Cells were treated with 1000 nM DW1350 in the absence or the presence of 100 nM $LTB_4$. The results are expressed as Mean±SD of the number of TRAP(+)MNCs ($n \geq 6$).

To elucidate the effect of DW1350 on $LTB_4$-induced osteoclast formation, 1000 nM of DW1350 was treated in the culture with or without $LTB_4$ (FIG. 4). Even in the single treatment, DW1350 could affect osteoclast formation and significantly inhibited it, similar to the results reported above. As described above in Culture Condition (A-2), simultaneous treatment and pre-treatment with DW1350 and $LTB_4$ showed a significant inhibition on $LTB_4$-stimulated osteoclast formation, which inhibitory activity was similar to that of single treatment. These results suggested that DW1350 showed similar effect on osteoclast differentiation regardless of $LTB_4$ existence.

Figure 5:
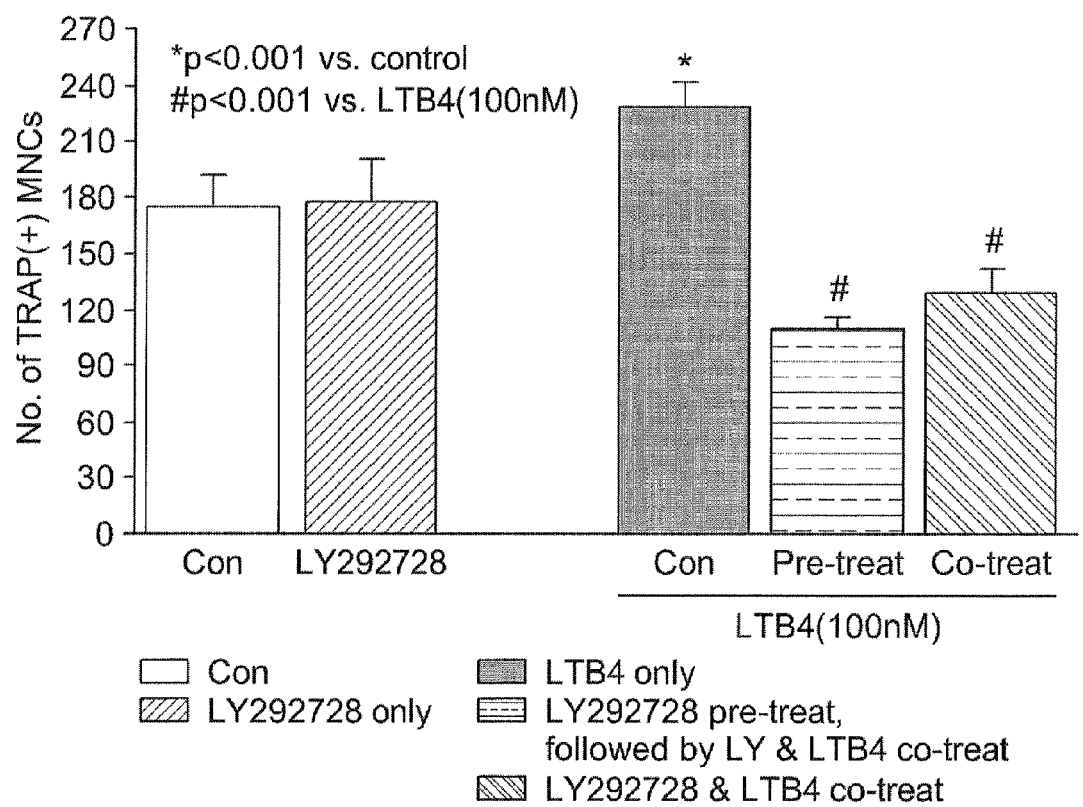
FIG. 5 shows the effect of LY292728 in $LTB_4$-induced osteoclast formation. An osteoclast containing cell suspension was plated on dentin slices. Three treatment regimens as described in A-2 were used. Cells were treated with 1000 nM LY292728 in the absence or the presence of 100 nM $LTB_4$. The results are expressed as Mean±SD of the number of TRAP(+)MNCs ($n \geq 6$).
Figure 6:
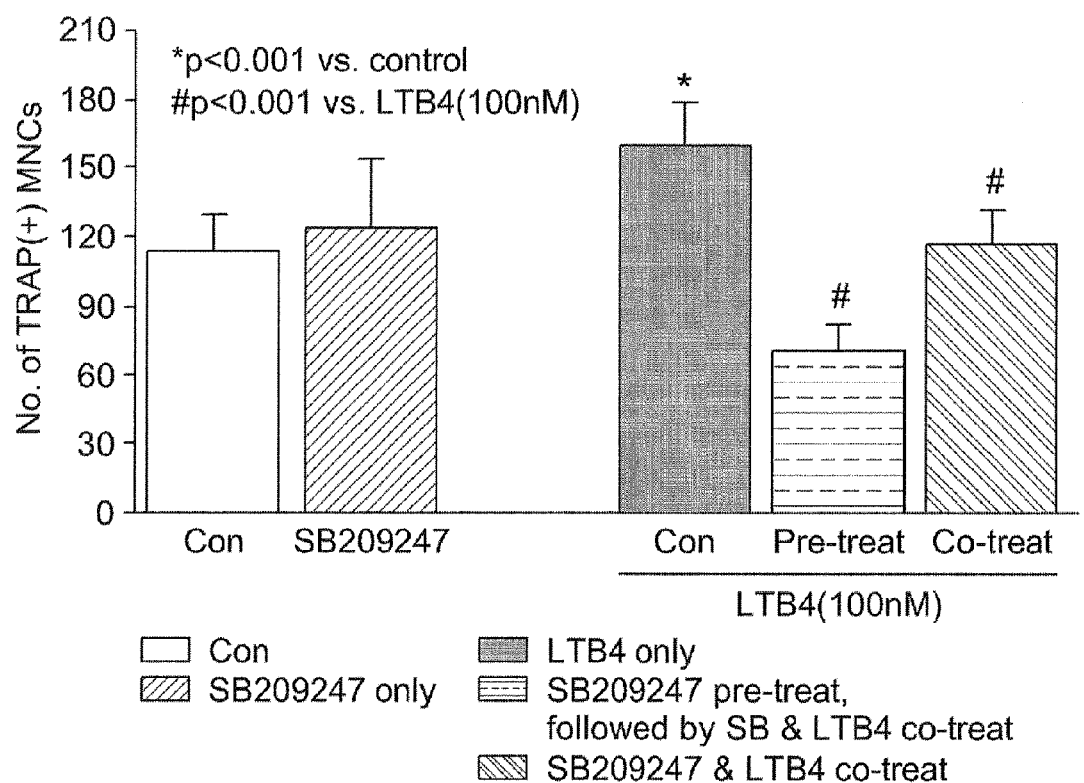
FIG. 6 shows the effect of SB209247 in $LTB_4$-induced osteoclast formation. An osteoclast containing cell suspension was plated on dentin slices. Three treatment regimens as described in A-2 were used. Cells were treated with 1000 nM SB209247 in the absence or the presence of 100 nM $LTB_4$. The results are expressed as Mean±SD of the number of TRAP(+)MNCs ($n \geq 6$).
Figure 7:
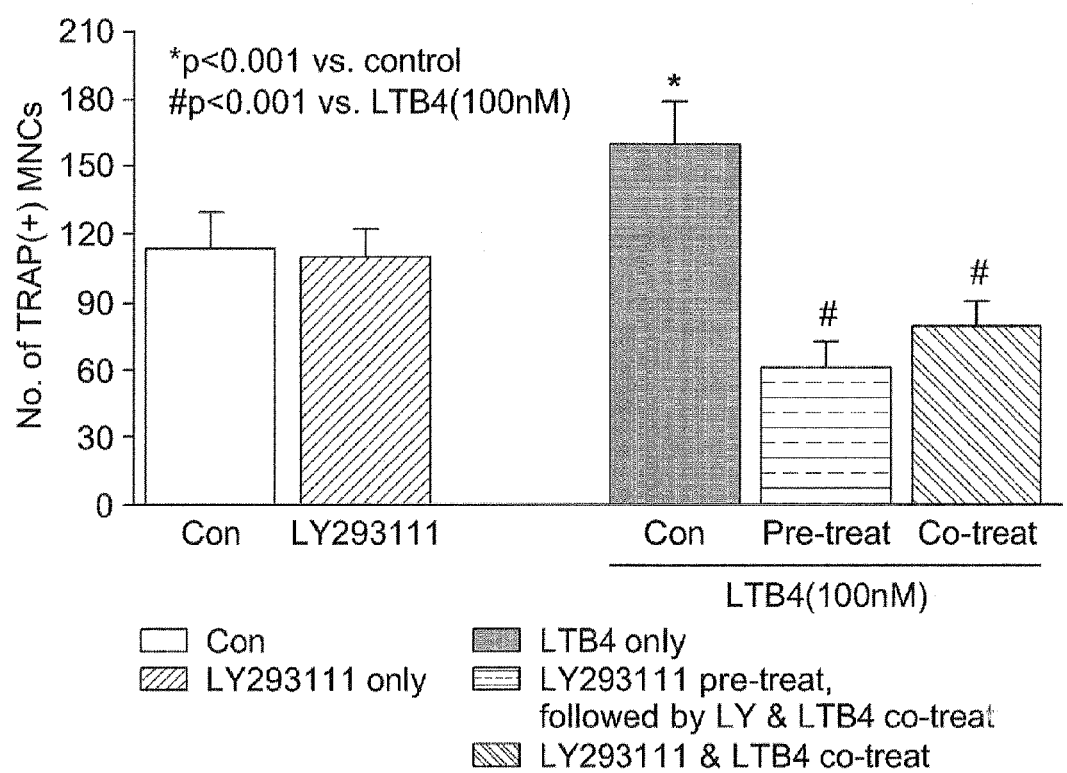
FIG. 7 shows the effect of LY293111 in $LTB_4$-induced osteoclast formation. An osteoclast containing cell suspension was plated on dentin slices. Three treatment regimens as described in A-2 were used. Cells were treated with 1000 nM LY293111 in the absence or the presence of 100 nM $LTB_4$. The results are expressed as Mean±SD of the number of TRAP(+)MNCs ($n \geq 6$).
Figure 8:
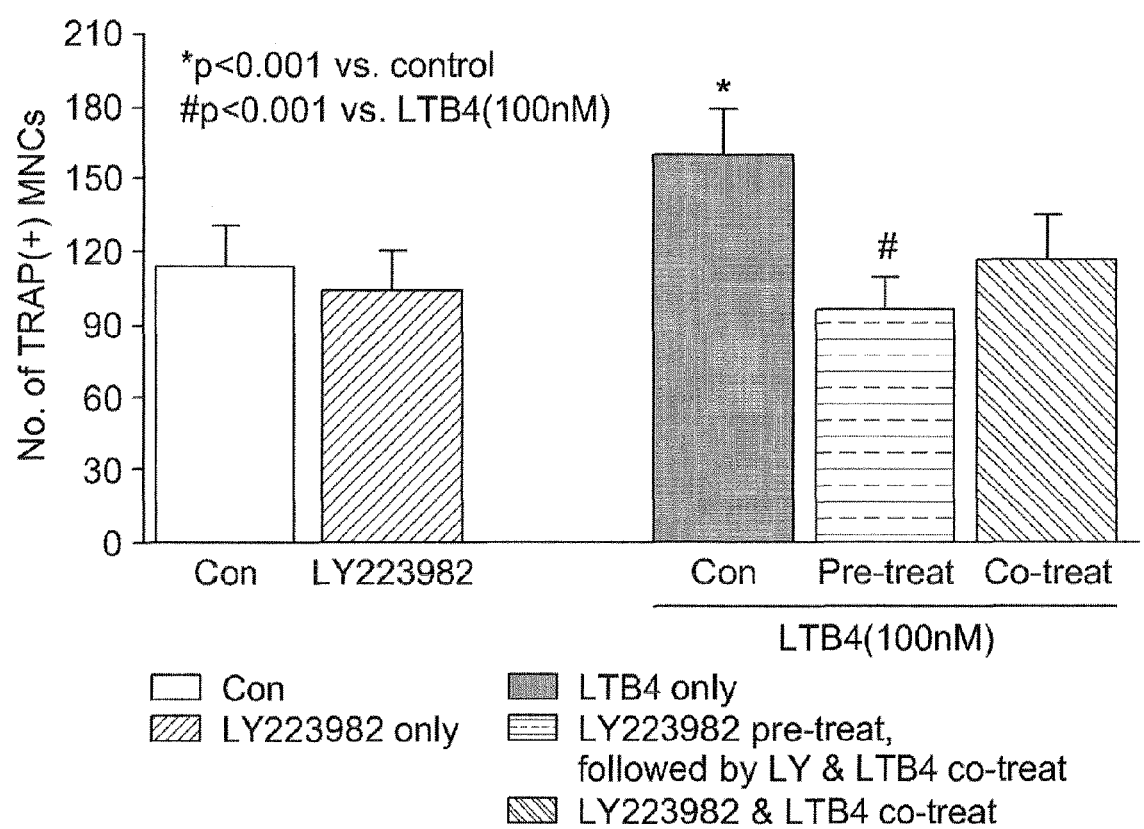
FIG. 8 shows the effect of LY223982 in $LTB_4$-induced osteoclast formation. An osteoclast containing cell suspension was plated on dentin slices. Three treatment regimens as described in A-2 were used. Cells were treated with 1000 nM LY223982 in the absence or the presence of 100 nM $LTB_4$. The results are expressed as Mean±SD of the number of TRAP(+)MNCs (n≧6).

Next, four potent $LTB_4$ receptor antagonists were investigated as to their effects on TRAP(+) osteoclast numbers in the presence of $LTB_4$. As shown in FIG. 5, the cultures treated with LY292728 alone at 1000 nM had no significant effect on osteoclast formation compared to the control culture. However, 100 nM $LTB_4$ treatment for 48 hours significantly increased the number of TRAP(+) MNCs with (40% increase). In the presence of $LTB_4$, simultaneous addition with LY292728 significantly abolished osteoclast formation increased by $LTB_4$. Pretreatment of osteoclasts with LY292728 followed by combined treatment of LY292728 and $LTB_4$ also appeared to suppress the formation of osteoclasts. Generally, the pretreatment of antagonists followed by simultaneous addition of antagonists and $LTB_4$ was more effective at decreasing numbers of TRAP(+) MNCs than the simultaneous treatment (co-treatment) with antagonists and $LTB_4$. Such activity of LY292728 on osteoclast formation induced by $LTB_4$ appeared to be similar in other $LTB_4$ receptor antagonists-treated cultures (FIGS. 6~8). The single treatment of SB209247, LY293111 and LY223982 did not change the number of osteoclasts, but these antagonists significantly abolished $LTB_4$-stimulated osteoclast formation.

3. Conclusion

In summary, we have discovered that LY292728, SB209247, LY293111 and LY223982, potent $LTB_4$ receptor antagonists, did not affect the osteoclast formation in the absence of $LTB_4$, but decreased the number of TRAP(+) MNCs in the presence of $LTB_4$. We believe this means that these antagonists function only in the presence of an agonist. However, in contrast, DW1350 by itself affects osteoclast formation regardless of $LTB_4$ existence. These results suggest that DW1350 would not belong to the category of typical $LTB_4$ receptor antagonists and might have an inhibitory activity on osteoclast formation through a unique feature.

EXAMPLE 7

Prophylactic Effects of the Compound

1. Prophylactic Effects of the Compound in Neurectomized ddY Mouse Model

An immobilization osteoporosis model using sciatic nerve neurectomized ddY mice is useful for evaluation of anti-osteoporotic drugs, because several parameters are clearly decreased by neurectomy within 2 or 3 weeks after operation. The effects of a drug would be based on histomorphometric changes of trabecular bone and thickness of cortical bone in this model. Alendronate (Fosamax), a nitrogen-containing bisphosphonate, is a potent inhibitor of bone resorption used for the treatment and prophylaxis of osteoporosis and the anti-osteoporotic effect of Fosamax in neurectomized mice were already reported.

The objective of the present study is to observe the anti-osteoporotic potential of DW1350MSA, and administration of the drug was initiated 2 days after neurectomy for prophylaxis study. The results were compared to that of Fosamax, well-documented anti-osteoporotic agents.

a) Materials and Method

1) Animals and Husbandry

Twenty-five female ddY mice (6-wk old upon receipt, SLC, Japan) were used after acclimatization for 7 days. Animals were allocated to 5 per polycarbonate cage in a temperature (20-25° C.) and humidity (30-35%) controlled room. Light:dark cycle was 12 hr:12 hr and feed (Samyang, Korea) and water were supplied free to access. 20 mice were neurectomized and 5 mice were sham operated. For the prophylaxis study, treatment was initiated 2 days after neurectomy and then each sample was administrated for 4 weeks.

2) Preparations and Administration of Drugs

DW1350MSA was dissolved in injectable distilled water and administered at a dosage volume of 10 ml/kg by oral gavage. The administered dose and schedule of these drugs are shown as Table 12.

TABLE 12

Experimental designs used in this study

| Group | Dose | Group ID | Vehicle | Route | Schedule |
|---|---|---|---|---|---|
| Sham | Sham | Sham | Injectable | Oral | once a |
| neurectomy | Control | Control | distilled | | day for |
| | Fosamax | F1 | water | | 4 weeks |
| | DW1350MSA | D10 | | | |
| | 10 ml/kg | | | | |
| | 10 ml/kg | | | | |
| | 1 mg/kg/10 ml | | | | |
| | 10 mg/kg/10 ml | | | | |
| | 50 mg/kg/10 ml | D50 | | | |

All test articles and vehicle were dosed by gastric gavage for 4 weeks
Operation was conduct under Ketamine and Xylazine anesthesia 3) Operation A. Sham operation: The right side of the sciatic nerve was exposed by incision of skin and hip muscles, (about 1 cm) after that closed by skin suture.

B. neurectomy: After exposure of the right side of the sciatic nerve, about 1 mm of sciatic nerve was removed. After that closed by routine methods.

C. Operation was conducted under Ketamine hydrochloride (M.W.=256.8; 23076-35-9, ICN Biochemicals Inc., USA) and Xylazine hydrochloride (M.W.=274.19; 116-00512, Wako Pure Chemical Industries Ltd., Japan) anesthesia.

4) Histological Procedures

The right side of tibia of mice were separated and fixed in 10% neutral buffered formalin (NBF), then decalcified in decalcifying solution [24.4% formic acid, and 0.5N sodium hydroxide] for 5 days. After that, embedded in paraffin, sectioned (3~4 um) and stained with hematoxylin-eosin strain.

5) Criteria Index

Mid-shaft cortical bone of tibia, and trabecular bone volume % of tibia were evaluated. In addition, histological profiles of epiphyseal regions of right tibia and femur were also observed.

A. Measurement of trabecular bone volume (TBV) Trabecular bone volume was calculated using automated image analysis (analySIS Image Processing; SIS, Germany) under magnification 100 (×200) of microscopy (Zeiss, Germany) in the uniform area of epiphyseal regions of the right tibia and/or femur (growth plate regions were excluded). Trabecular bone volume was calculated as percentage levels.

B. Thickness of cortical bone (Cbt): Cortical bone thickness was detected in mid-shaft regions of right tibia and/or femur, and they were calculated using an automated image analyzer (analysis Image Processing; SIS, Germany) under magnification 200 (×200) of microscopy (Zeiss, Germany) at prepared histological samples. The thickness was detected as um levels.

C. Histological profiles: The changes of histological profiles of right tibia were demonstrated under Hematoxylin-Eosin strain.

6) Statistical Analyses

All data was calculated as mean±S.D. Statistical analyses was conducted using Mann-Whitney U-Wilcoxon Rank Sum W test (M-W test) with SPSS for Windows (Release 6.1.3., SPSS Inc., USA).

b) Results and Discussion

1) Trabecular Bone Volume % (TBV)

Figure 9:
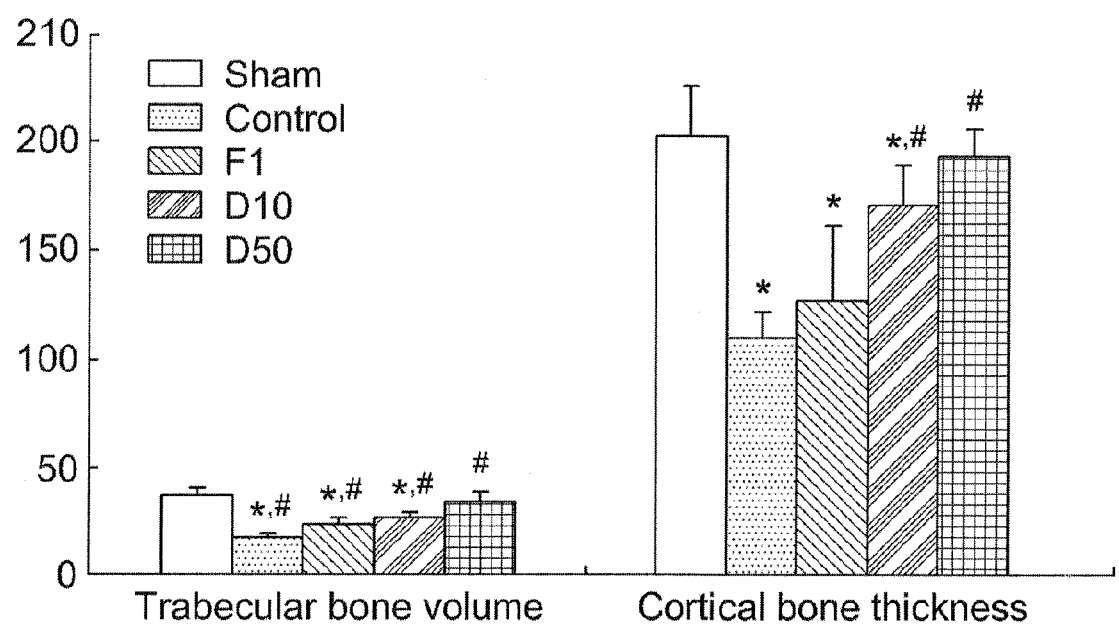
FIG. 9 shows changes of trabecular bone volume (%) at epiphyseal regions and cortical bone thickness (μm) at midshaft regions of right tibia in a neurectomized ddY mouse model. n=5; (Mean±S.D); F1, Fosamax 1 mg/kg-dosing group; D10, DW1350MSA 10 mg/kg-dosing group; D50, DW1350MSA 50 mg/kg-dosing group; Trabecular bone volume and Cortical bone thickness were calculated using automated image analyzer (analySIS Image Processing; SIS, Germany); *p<0.01 compared to that of Sham group by M-W test; #p<0.01 compared to that of Control group by M-W test.

TBV % after neurectomy and drug administration were summarized in Table 13 and FIG. 9. A significant (p<0.01) decrease of TBV % in all experimental groups compared to that of the Sham group was detected after neurectomy in the right side of the tibia except for the DW1350MSA 50 mg/kg-dosing group that was similar to that of the Sham group. TBV % in the right side of the tibia in the Fosamax 1 mg/kg-dosing groups were significantly (p<0.01) increased compared to that of the control group. In addition, a significant dose-dependent (p<0.01) increase of trabecular bone volume % in the DW1350MSA-dosing groups was also demonstrated compared to that of the control group and increasing ratios were greater than that of the Fosamax-dosing group.

In summary, it is considered that Fosamax and DW1350MSA has some significant effect on TBV %.

TABLE 13

Changes of TBV at epiphyseal regions and cortical bone thickness at mid-shaft regions of right tibia

| Group | TBV (%)[1] | Cbt (um)[1] |
|---|---|---|
| Sham | 36.96 ± 3.22 | 201.86 ± 24.76 |
| Control | 16.24 ± 1.38* | 109.34 ± 12.48* |
| Fosamax 1 mg/kg | 21.81 ± 4.35*, # | 125.75 ± 36.01* |
| DW1350MSA 10 mg/kg | 25.75 ± 2.87*, # | 171.36 ± 18.60*, # |
| DW1350MSA 50 mg/kg | 33.29 ± 4.96# | 193.87 ± 12.50# | n = 5; (Mean ± S.D., g);
[1]Trabecular bone volume and Cortical bone thickness were calculated using automated image analyzer (analysis Image Processing; SIS, Germany);
*p < 0.01 compared to that of Sham group by M-W test;
p < 0.01 compared to that of Control by M-W test.

2) Thickness of Cortical Bone

The thickness of the cortical bone after neurectomy and drug administration were summarized in Table 13 and FIG. 9. A significant (p<0.01) decrease of cortical bone (compact bone) thickness in all experimental groups compared to that of the Sham group was detected after neurectomy in the right side of the tibia except for the DW1350MSA 50 mg/kg-dosing group that was similar to that of the Sham group. Cortical bone thickness of the right side of tibia in the Fosamax 1 mg/kg-dosing groups were significantly increased compared to that of the control group but significances were not demonstrated. However, a significant dose-dependent (p<0.01) increase of cortical bone thickness in the DW1350 MSA-dosing groups was demonstrated compared to that of the control group and the increasing rate was greater than that of the Fosamax-dosing group.

In summary, it is considered that Fosamax and DW1350MSA has some significant effect on cortical bone thickness.

3) Histological Profiles

Figure 10:
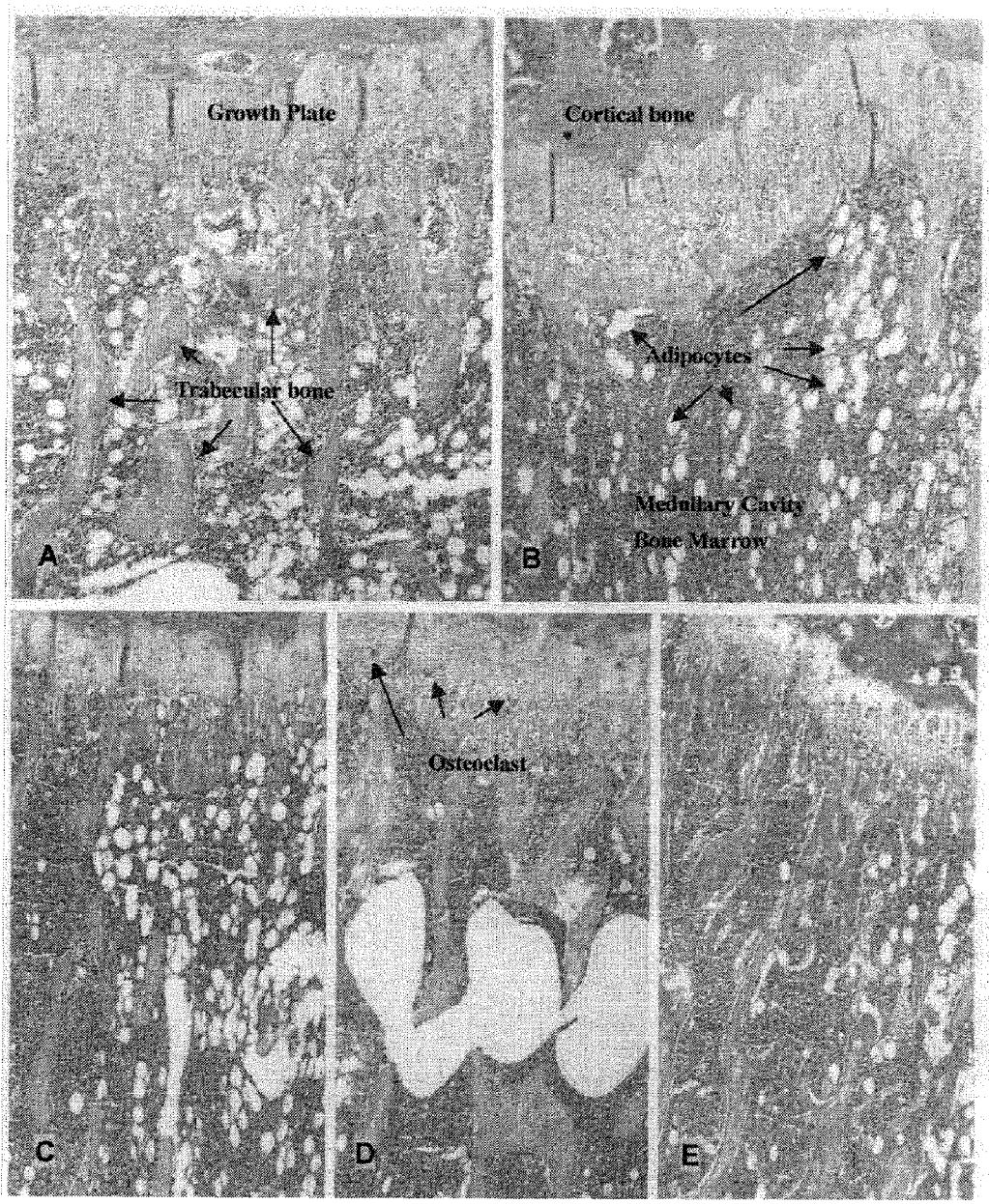
FIG. 10 shows histological profiles of epiphyseal regions of right tibia in a neurectomized ddY mouse model. A, Sham group; B, Control group; C, Fosamax 1 mg/kg-dosing group; D, DW1350MSA 10 mg/kg-dosing group; E, DW1350MSA 50 mg/kg-dosing group; A-E, Hematoxylin-Eosin Stain, X 60.

The histological profiles of epiphyseal regions of right tibia and femur were showed in FIG. 10. Relatively well-developed trabecular bone which was extended from growth plate to intra-medullary cavity, was demonstrated in Sham group (FIG. 10A). However, in a case of Control, extended trabecular bone was rarely seen (FIG. 10B). In Fosamax and DW1350MSA-dosing groups, more numerous extended trabecular bones were demonstrated compared to that of Control group (FIG. 10C~E) but their width and number was somewhat lower than that of Sham group. Compared to that of Fosamax 1 mg/kg-dosing group, relatively well developed, especially in width and number, trabecular bone was detected in DW1350MSA treated group. In addition, somewhat dose-dependency was also observed in a case of DW1350MSA-dosing groups.

c) Conclusion

From above results, it appeared that the effective dosage of DW1350MSA is somewhat higher than that of Fosamax. However, considered the serious toxicological problem of Fosamax such as severe esophagitis, disorder of kidney, liver damage, hypocalcaemia and related muscle tetany and so on, it is enough effective dosage to use in prophylaxis of immobilization osteoporosis. In conclusion, it should be suggested that DW1350MSA has enough and favorable effect to prophylaxis of immobilization osteoporosis.

2. Prophylactic Effects of the Compound in Ovariectomized ddY Mouse Model

Estrogen-deficient ovariectomized osteoporosis model using ddY mice is a useful for evaluation of anti-osteoporotic drugs, because several parameters are clearly decreased by ovariectomy within 4 to 6 weeks after operation. The effects of a drug would be based on histomorphometric changes of trabecular bone and thickness cortical bone in this model.

Alendronate (Fosamax), a nitrogen-containing bisphosphonate, is a potent inhibitor of bone resorption used for the treatment and prophylaxis of osteoporosis and the anti-osteoporotic effect of Fosamax in the ovariectomized were already reported.

The objective of present study is to observe the prophylactic effect of DW1350MSA, and administration of drug was initiated 3 days after ovariectomy for prophylaxis study. The results were compared to that of Fosamax, well-documented anti-osteoporotic agents.

a) Materials and Method

1) Animals and Husbandry

Twenty-five female ddY mice (6-wk old upon receipt, SLC, Japan) were used after acclimatization for 7 days. Animals were allocated 5 per polycarbonate cage in a temperature (20-25° C.) and humidity (30-35%) controlled room. Light:dark cycle was 12 hr:12 hr and feed (Samyang, Korea) and water were supplied free to access. 20 mice were ovariectomized and 5 mice were sham operated. For prophylaxis study, treatment was initiated 3 days after ovariectomy and then each sample was administrated for 6 weeks.

2) Preparations and Administration of Drugs

DW1350MSA was dissolved in injectable distilled water and administered at a dosage volume of 10 ml/kg by oral gavage. The administered dose and schedule of these drugs were showed as Table 14.

3) Operation

A. Sham operation: Bilateral ovaries were exposed by incision of skin and abdominal muscles, (about 3 cm) after that closed by skin suture.

B. Ovariectomy: After exposure of bilateral ovaries, they were removed. After that closed by routine methods.

C. Operation was conduct under Ketamine hydrochloride (M.W.=256.8; 23076-35-9, ICN Biochemicals Inc., USA) and Xylazine hydrochloride (M.W.=274.19; 116-00512, Wako Pure Chemical Industries Ltd., Japan) anesthesia.

4) Histological Procedures

The right side of tibia and femur of each mouse were separated and fixed in 10% neutral buffered formalin (NBF), then decalcified in decalcifying solution [24.4% formic acid, and 0.5N sodium hydroxide] for 5 days. After that, embedded in paraffin, sectioned (3~4 um) and stained with hematoxylin-eosin stain.

5) Criteria Index

Histomorphometric changes of tibia and femur were evaluated. All histomorphometric indices including trabecular bone volume (TBV, %), thickness of trabecular bone (Tbt), trabecular bone number (Tbn), and length of trabeculer bone (Tbl) were calculated using automated image analysis (analysis Image Processing; SIS, Germany) under magnification 200 (×200) of microscopy (Zeiss, Germany) in the epiphyseal regions of right tibia and/or femur. In addition, cortical bone thickness (Cbt) was measured in mid-shaft region of right tibia and femur. Osteoclast cell numbers (Ocn) were calculated as seen under 20000 $\mu m^2$ of epiphyseal regions using automated image analyzer.

A. Measurement of trabecular bone volume (TBV): Trabecular bone volume was calculated using automated image analysis in the uniform area of epiphyseal regions of right tibia and/or femur (growth plate regions were excluded). Trabecular bone volume was calculated as percentage levels.

B. Measurement of histomorphometric index of trabecular bone: Thickness of trabecular bone (Tbt), trabecular bone number (Tbn), and length of trabecular bone (Tbl) were calculated using automated image analysis in the epiphyseal regions of right tibia and/or femur. Tbt and Tbl were calculated as um levels, and Tbn were calculated as number/whole sectional part of epiphyseal regions levels.

C. Thickness of cortical bone (Cbt): Cortical bone thickness was detected in mid-shaft regions of right tibia and/or femur, and they were calculated using automated image analyzer at prepared histological samples. The thickness was detected as um levels.

D. Osteoclast cell number (Ocn): Osteoclast cell numbers were calculated as seen in epiphyseal regions using automated image analyzer at prepared histological samples.

TABLE 14

Experimental designs used in this study

| Group | | Dose | Group ID | Vehicle | Route | Schedule |
|---|---|---|---|---|---|---|
| Sham ovariectomy | Sham | 10 ml/kg | Sham | Injectable distilled water | Oral | Once a day for 6 weeks |
| | Control | 10 ml/kg | Control | | | |
| | Fosamax | 10 mg/kg/10 ml | F10 | | | |
| | DW1350MSA | 10 mg/kg/10 ml | D10 | | | |
| | | 50 mg/kg/10 ml | D50 | | | |

E. Histological profiles: The changes of histological profiles of right tibia and/or femur were demonstrated under Hematoxylin-Eosin strain.

6) Statistical Analyses

All data was calculated as mean±S.D. Statistical analyses was conducted using Mann-Whitney U-Wilcoxon Rank Sum W test (M-W test) with SPSS for Windows (Release 6.1.3., SPSS Inc., USA).

b) Results and Discussion

1) Trabecular Bone Volume (TBV)

Histomorphometric changes after ovariectomy and drug administration were summarized in Table 15 and 16. In the Tibia, a significant ($p<0.01$) decreases of TBV in all experimental groups compared to that of Sham were detected after ovariectomy. However, TBV in F10 were significantly increased compared to that of Control group. In addition, significant increase of TBV was also demonstrated in D10 and D50 with dose-dependent patterns compared to that of Control group but increasing ratios were somewhat lower than that of F10. In the Femur, a significant ($p<0.01$) decrease of TBV in all experimental groups compared to that of Sham were detected after ovariectomy except for F10, which showed similar values to Sham. However, TBV in F10 were significantly increased compared to that of Control group. In addition, significant increase of TBV was also demonstrated in D10 and D50 with dose-dependent manners compared to that of Control group but increasing ratios were somewhat lower than of F10.

Summarized above-mentioned, it is considered that DW1350MSA has some significance effect to inhibit the decrease of TBV induced by ovariectomy but the efficacy was somewhat lower than that of Fosamax.

TABLE 15

Histomorphometric changes of trabecular and cortical bone at epiphyseal regions and/or mid-shaft regions of right tibia with osteoclast cell number

| Group | Sham | Control | F10 | D10 | D50 |
|---|---|---|---|---|---|
| TBV[1] | 57.24 ± 7.43 | 15.99 ± 3.96* | 47.56 ± 7.23**, # | 35.20 ± 4.90*, # | 38.42 ± 4.67*, # |
| Tbt[2] | 140.00 ± 20.54 | 16.80 ± 4.76* | 83.20 ± 39.86**, # | 60.80 ± 13.20*, # | 112.60 ± 45.76# |
| Tbn[3] | 18.60 ± 2.70 | 2.60 ± 1.14* | 12.60 ± 4.98# | 11.80 ± 3.11**, # | 11.80 ± 3.96**, # |
| Tbl[4] | 924.60 ± 66.63 | 213.40 ± 190.97* | 550.00 ± 74.98*, ## | 605.00 ± 160.44*, ## | 679.20 ± 249.47## |
| Cbt[5] | 208.80 ± 13.85 | 47.80 ± 10.73* | 59.80 ± 15.55* | 136.80 ± 26.58*, # | 170.40 ± 44.73# |
| Ocn[6] | 1.60 ± 0.89 | 10.60 ± 2.07* | 9.40 ± 2.30* | 5.40 ± 1.52, # | 3.60 ± 1.14, # | n = 5; (Mean ± S.D.); Group ID was listed in Table 14;
[1]TBV, trabecular bone volume (Unit, %);
[2]Tbt, trabecular bone thickness (Unit, um);
[3]Tbn, trabecular bone number (Unit, number/epiphyseal);
[4]Tbl, trabecular bone length (Unit, um);
[5]Cbt, cortical bone thickness (Unit, um);
[6]Ocn, osteoclast cell number(Unit, number).
*$p < 0.01$ compared to that of sham by M-W test;
**$p < 0.05$ compared to that of Sham by M-W test;
$p < 0.01$ compared to that of Control by M-W test;
$p < 0.05$ compared to that of Control by M-W test.

TABLE 16

Histomorphometric changes of trabecular and cortical bone at epiphyseal regions and/or mid-shaft regions of right femur with osteoclast cell numbers

| Group | Sham | Control | F10 | D10 | D50 |
|---|---|---|---|---|---|
| TBV[1] | 57.52 ± 7.98 | 17.24 ± 4.72* | 58.26 ± 5.77# | 36.97 ± 9.59*, # | 41.91 ± 6.04*, # |
| Tbt[2] | 74.00 ± 25.17 | 29.80 ± 5.89* | 33.00 ± 12.45** | 48.60 ± 10.50**, ## | 68.00 ± 21.41# |
| Tbn[3] | 18.00 ± 3.87 | 4.00 ± 1.22* | 23.60 ± 2.97**, # | 19.00 ± 1.58# | 21.80 ± 1.92# |
| Tbl[4] | 762.00 ± 165.92 | 156.20 ± 95.99* | 460.80 ± 260.64**, ## | 635.60 ± 190.76# | 743.40 ± 187.00# |
| Cbt[5] | 142.80 ± 22.96 | 46.60 ± 21.52* | 53.00 ± 23.82* | 118.00 ± 16.79# | 140.26 ± 33.16# |
| Ocn[6] | 2.80 ± 1.48 | 11.20 ± 3.96* | 9.40 ± 1.14* | 5.00 ± 1.58# | 4.40 ± 1.34# | n = 5; (Mean ± S.D.); Group ID was listed in Table 14;
[1]TBV, trabecular bone volume (Unit, %);
[2]Tbt, trabecular bone thickness (Unit, um);
[3]Tbn, trabecular bone number (Unit, number/epiphyseal);
[4]Tbl, trabecular bone length (Unit, um);
[5]Cbt, cortical bone thickness (Unit, um);
[6]Ocn, osteoclast cell number(Unit, number).
*$p < 0.01$ compared to that of sham by M-W test;
**$p < 0.05$ compared to that of Sham by M-W test;
$p < 0.01$ compared to that of Control by M-W test;
$p < 0.05$ compared to that of Control by M-W test.

2) Trabecular Bone Thickness (Tbt)

In the Tibia, a significant ($p<0.01$) decrease of Tbt in all ovariectomized groups compared to that of Sham were detected except for D50, which showed similar values to Sham. However, Tbt in F10 and DW1350MSA-dosing groups were significantly increased compared to that of Control group. In addition, significantly increase of Tbt was demonstrated in dose-dependent patterns in case of DW1350MSA dosing groups. In the Femur, a significant ($p<0.01$) decrease of Tbt in all experimental groups compared to that of Sham were detected except for D50, which showed similar values to Sham. However, a significantly increase of Tbt was observed in D10 and D50 with dose dependent manners compared to that of Control group, but no significances were demonstrated in F10 compared to that of Control group.

Summarized above-mentioned, it is considered that DW1350MSA has significance effect to inhibit the decrease of Tbt induced by ovariectomy and the efficacy was somewhat higher than that of Fosamax.

3) Trabecular Bone Number (Tbn)

In the Tibia, a significant decrease of Tbn in all ovariectomized groups compared to that of Sham were detected except for F10, which were also showed somewhat lower values compared to that of Sham but significances were not detected. Reversed to Sham, Tbn in F10 and DW1350MSA-dosing groups were significantly increased compared to that of Control group. However, increase of Tbn in DW1350MSA-dosing groups wasn't showed dose-dependent patterns. In the Femur, a significant decrease of Tbn in Control compared to that of Sham was detected. However, a significant increase of Tbn was observed in all tested groups with dose-dependent manners compared to that of Control. The Tbn in F10 showed more numerous than that of sham, but this effect was not demonstrated in DW1350MSA-dosing groups.

Summarized above-mentioned, it is considered that DW1350MSA has significance effect to inhibit the decrease of Tbn induced by ovariectomy and the efficacy was somewhat lower than that of Fosamax.

4) Trabecular Bone Length (Tbl)

In the Tibia, significant decreases of Tbl in all ovariectomized groups compared to that of Sham were detected except for D50, which showed similar values to Sham. However, Tbl in F10 and DW1350MSA-dosing groups were significantly increased compared to that of Control group. In addition, significant increase of Tbl was demonstrated in dose-dependent patterns in case of DW1350MSA-dosing groups. In the Femur, significant decreases of Tbl in all experimental groups compared to that of Sham were detected except for DW1350MSA-dosing groups, which showed similar values to Sham. However, a significant increase of Tbl was observed in F10, and DW1350MSA-dosing groups with dose-dependent manners compared to that of Control group. The increase ratio in DW1350MSA-dosing groups was higher than that of F10.

Summarized above-mentioned, it is considered that DW1350MSA has significant effect to inhibit the decrease of Tbl induced by ovariectomy and the efficacy was somewhat higher than that of Fosamax.

5) Cortical Bone Thickness (Cbt)

In the Tibia, significant decreases of Cbt in all ovariectomized groups compared to that of Sham were detected except for D50, which was showed slight decreased values compared to that of Sham but significances were not detected. However, Cbt in DW1350MSA-dosing groups was significantly increased compared to that of Control with dose-dependent patterns, but no significances were demonstrated in F10 compared to that of Control group. In the Femur, a significant decrease of Cbt in Control and F10 groups compared to that of Sham were detected. However, in case of DW1350MSA-dosing groups, a significant increase of Cbt was observed with dose-dependent manners compared to that of Control, but no significances were demonstrated in F10 compared to that of Control group. The values in DW1350MSA-dosing groups were similar to that of Sham.

Summarized above-mentioned, it is considered that DW1350MSA has significant effect to inhibit the decrease of Cbt induced by ovariectomy and the efficacy was higher than that of Fosamax, which was showed no favorable effect to changes of Cbt.

6) Osteoclast Cell Number (Ocn)

In the Tibia, significant increases of Ocn in all ovariectomized groups compared to that of Sham were detected. However, Ocn in DW1350MSA-dosing groups was significantly decreased compared to that of Control with dose-dependent patterns, but no significances were demonstrated in F10 compared to that of Control group. In the Femur, a significant increase of Ocn in Control and F10 groups compared to that of Sham were detected. In case of DW1350MSA-dosing groups, slight increased values were also observed compared to that of Sham but significances were not detected. However, a significant decrease of Ocn was observed in DW1350MSA-dosing groups with dose-dependent manners compared to that of Control, but no significances were demonstrated in F10 compared to that of Control group.

Summarized above-mentioned, it is considered that DW1350MSA has significant effect to inhibit the increase of Ocn induced by ovariectomy and the efficacy was higher than that of Fosamax, which was showed no favorable effect to changes of Ocn.

7) Histological Profiles

Figure 11:
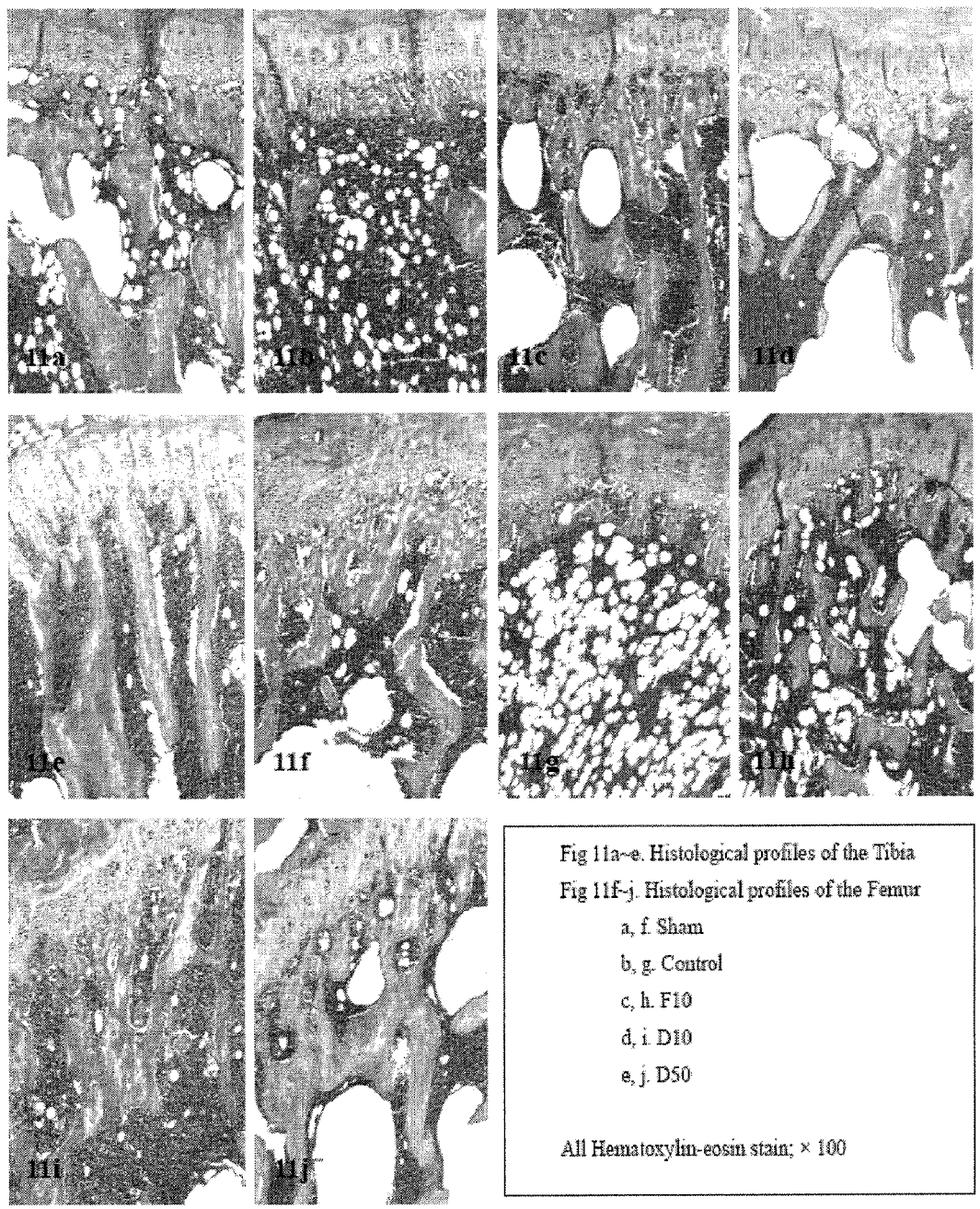
FIG. 11 shows histological profiles of epiphyseal regions in ovariectomized ddY mouse model.
Figure 12:
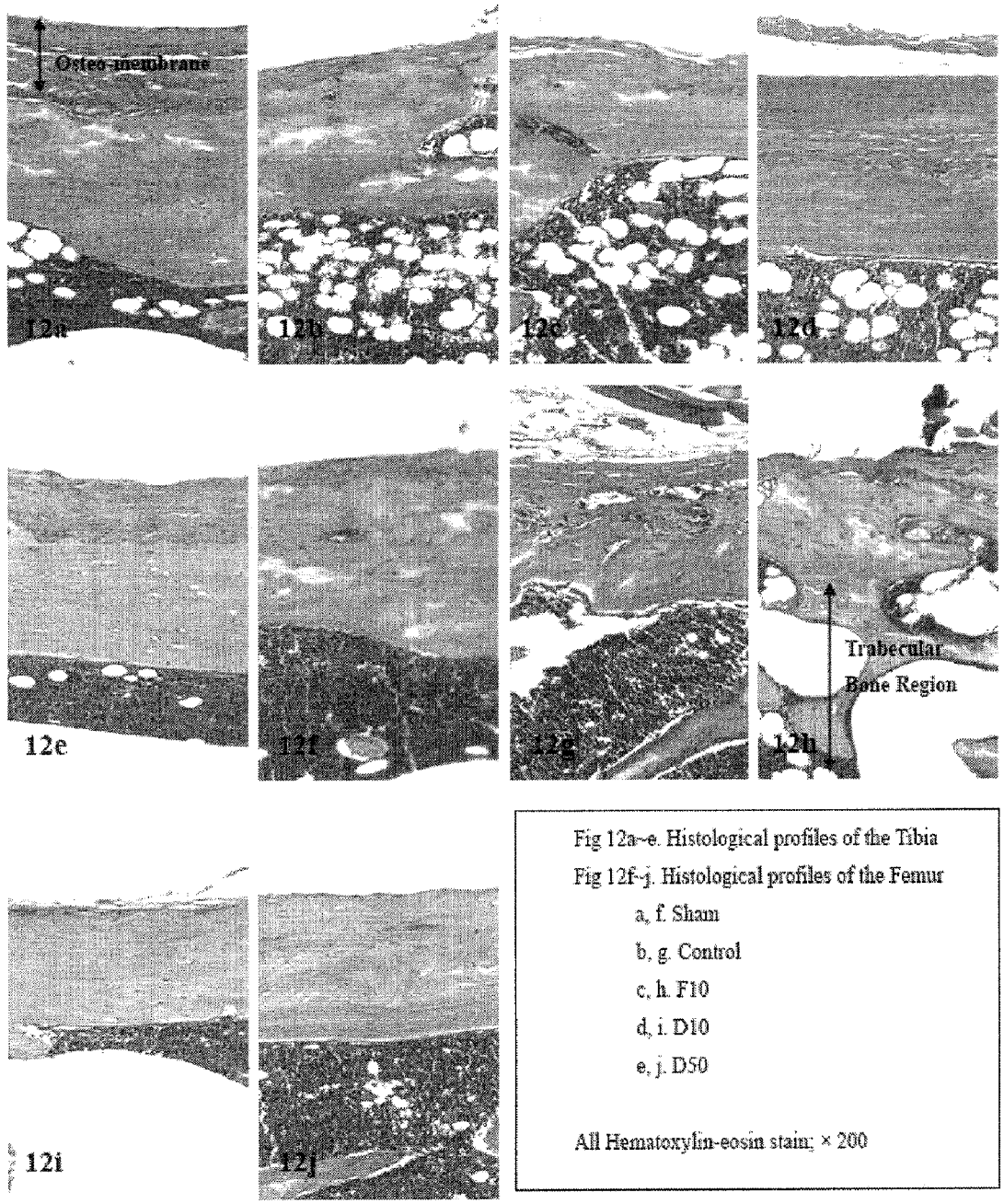
FIG. 12 shows histological profiles of cortical bone regions in ovariectomized ddY mouse model.

The histological profiles of "Epiphyseal regions" of right tibia and femur were showed in FIG. 11. Relatively well-developed trabecular bone which was extended from growth plate to intra-medullary cavity, was demonstrated in Sham. However, in a case of Control, extended trabecular bone was rarely seen. In F10 and DW1350MSA-dosing groups, more numerous extended trabecular bones were demonstrated compared to that of Control but their width and number was somewhat lower than that of Sham. Compared to that of F10, relatively well developed, especially in width and length, trabecular bone was detected in DW1350MSA-dosing groups with somewhat dose-dependency. The histological profiles of "Cortical bone" of right tibia and femur were showed in FIG. 12. Well-developed osteo-membrane and compact bones were demonstrated in Sham. However, narrowing of total width of cortical bone was detected in Control group. In addition, large holes containing cells like bone marrow cells were also demonstrated in this group. Similar width and histological profiles were demonstrated in Fosamax-dosing groups, the width and compactness of cortical bones were dramatically increased compared to that of Control but their width and compactness were somewhat lower than that of Sham. In addition, the holes just as detected in Control groups were also demonstrated in F10 but these holes were dose-dependently decreased in DW1350MSA-dosing groups.

c) Conclusion

From above results, it appeared that the effective dosage of DW1350MSA is somewhat higher than that of Fosamax. However, considered the serious toxicological problem of Fosamax such as severe esophagitis, disorder of kidney, liver damage, hypocalcaemia and related muscle tetany and so on, it is enough effective dosage to use in prophylaxis of estrogen-deficient osteoporosis induced by ovariectomy. In addition, DW1350MSA has more favorable effect to inhibit the changes of various histomorphometric indices compared to that of Fosamax except for trabecular bone volume and numbers, in those indices it showed similar or superior to that of Sham.

In conclusion, it should be suggested that DW1350MSA has more favorable effect to prophylaxis of estrogen-deficient osteoporosis induced by ovariectomy than that of Fosamax.

Industrial Applicability

The aforementioned examples have revealed that both DW1350 and DW1352 exert better inhibitory effect against osteoclast in terms of differentiation, formation, fusion and bone absorption.

Both agents may prove to be effective for the prophylaxis and treatment of osteoporosis, since they can suppress the osteoclastic function with enhanced stimulation of osteoblastic activity, compared to DW1349 and DW1351 with the structural similarity, as well as HS1141 and CGS-25019C.

Therefore, it is expected that the compound of the present invention may provide the basis for new osteoporosis therapies aimed at suppressing the osteoclastic bone resorption and stimulating the osteoblastic bone formation.

The invention claimed is:

1. A method for the prophylaxis of osteoporosis in a subject, the method comprising administering a composition comprising the compound of following formula 1 or a salt thereof to the subject in an amount effective to inhibit osteoclast activity and to stimulate osteoblast activity:

Formula 1

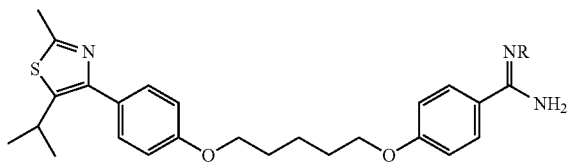

Wherein, R is a hydroxy group and wherein in an in vitro Pit Formation Assay, without the addition of Leukotriene-B4 (LTB4), said compound inhibits osteoclast activity.

2. A method for the prophylaxis of osteoporosis in a subject, the method comprising administering a composition comprising the compound of following formula 1 or a salt thereof to the subject in an amount effective to inhibit osteoclast activity and to stimulate osteoblast activity:

Formula 1

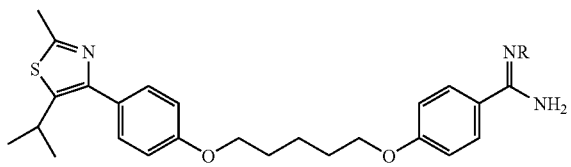

Wherein, R is a hydroxy group, and wherein in an in vitro Alkaline Phosphatase Assay, without the addition of Leukotriene-$B_4$ (LTB$_4$) said compound stimulates osteoblast activity.

3. A method for the prophylaxis of osteoporosis in a subject, the method comprising administering a composition comprising the compound of following formula 1 or a salt thereof to the subject in an amount effective to inhibit osteoclast activity and to stimulate osteoblast activity:

Formula 1

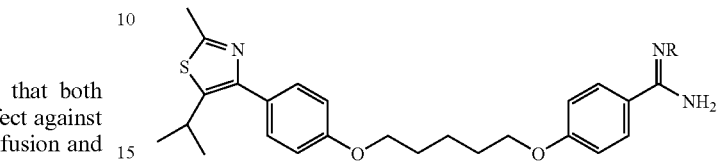

Wherein, R is a hydroxy group, and wherein in an in vitro Cell Fusion Assay, without the addition of Leukotriene-B$_4$ (LTB$_4$) said compound inhibits osteoclast activity.

4. A method for the prophylaxis of osteoporosis in a subject, the method comprising administering a composition comprising the compound of following formula 1 or a salt thereof to the subject in an amount effective to inhibit osteoclast activity and to stimulate osteoblast activity:

Formula 1

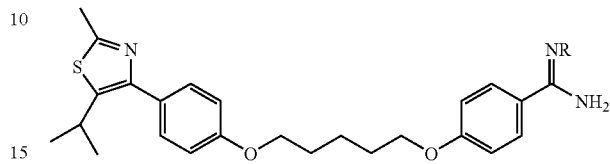

Wherein, R is a hydroxy group, and wherein in an in vitro Tartarate Resistance Acid Phosphatase (TRAP) Staining Assay, without the addition of Leukotriene-B$_4$ (LTB$_4$) said compound inhibits osteoclast activity.

5. A method for the prophylaxis of osteoporosis in a subject, the method comprising administering a composition comprising the compound of following formula 1 or a salt thereof to the subject in an amount effective to inhibit osteoclast activity and to stimulate osteoblast activity:

Formula 1

Wherein, R is a hydroxy group, wherein in an in vivo Assay, said compound inhibits the decrease of TBV (trabecular bone volume) and, Tbt (trabecular bone thickness), Tbn (trabecular bone number), Tbl (trabecular bone length) and Cbt (cortical bone thickness) induced by ovariectomy and the increase of Ocn (Osteoclast cell number) induced by ovariectomy.

6. A method for the prophylaxis of osteoporosis in a subject, the method comprising administering a composition comprising the compound of following formula 1 or a salt thereof to the subject in an amount effective to inhibit osteoclast activity and to stimulate osteoblast activity:

Formula 1

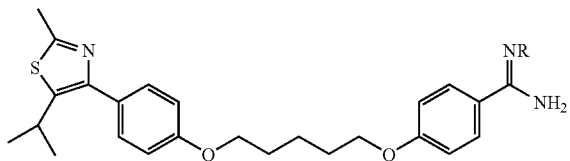

Wherein, R is a hydroxy group, wherein in an in vivo Assay, said compound inhibits the decrease of TBV (trabecular bone volume) and Cbt (cortical bone thickness) induced by neurectomy.

7. The method of any of claims 1 and 2 to 6, wherein the compound is N-hydroxy-4-{5-[4-(5-isopropyl-2-methyl-1,3-thiazol-4-yl)phenoxy]pentoxy}-benzamidine methane sulfonate.

* * * * *